US007374895B2

(12) United States Patent
Itadani et al.

(10) Patent No.: US 7,374,895 B2
(45) Date of Patent: May 20, 2008

(54) GUANOSINE TRIPHOSPHATE (GTP) BINDING PROTEIN-COUPLED RECEPTOR PROTEINS THAT BIND HISTAMINE AND ARE EXPRESSED IN THE BRAIN

(75) Inventors: Hiraku Itadani, Ibaraki (JP); Tetsuo Takimura, Ibaraki (JP); Takao Nakamura, Ibaraki (JP); Masahiko Kobayashi, Ibaraki (JP); Ken-Ichi Tanaka, Ibaraki (JP); Yusuke Hidaka, Ibaraki (JP); Masataka Ohta, Ibaraki (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/447,407

(22) Filed: Jun. 6, 2006

(65) Prior Publication Data

US 2007/0015220 A1    Jan. 18, 2007

Related U.S. Application Data

(60) Division of application No. 10/759,463, filed on Jan. 16, 2004, now Pat. No. 7,074,594, which is a division of application No. 09/891,053, filed on Jun. 25, 2001, now Pat. No. 6,750,322, which is a continuation-in-part of application No. PCT/JP99/07280, filed on Dec. 24, 1999.

(30) Foreign Application Priority Data

Dec. 25, 1998 (WO) ................. PCT/JP98/05967
May 25, 1999 (JP) ........................... 11/145661

(51) Int. Cl.
    *G01N 33/566* (2006.01)
(52) U.S. Cl. .............. 435/7.21; 435/7.2; 436/501
(58) Field of Classification Search ............. 435/7.21
    See application file for complete search history.

(56) References Cited

U.S. PATENT DOCUMENTS

| 4,767,778 | A | 8/1988 | Arrang et al. |
| 5,194,596 | A | 3/1993 | Tischer et al. |
| 5,342,960 | A | 8/1994 | Garbarg et al. |
| 5,882,893 | A | 3/1999 | Goodearl |
| 6,093,545 | A | 7/2000 | Goodearl et al. |
| 6,750,322 | B2 | 6/2004 | Itadani et al. |
| 7,074,594 | B2 | 7/2006 | Itadani et al. |
| 2005/0234223 | A1 | 10/2005 | Kotani et al. |
| 2007/0015220 | A1 | 1/2007 | Itadani et al. |

FOREIGN PATENT DOCUMENTS

| WO | WO 91/17146 | 11/1991 |
| WO | WO 99/28470 | 6/1999 |
| WO | WO 99/33978 | 7/1999 |
| WO | WO 00/20011 | 4/2000 |
| WO | WO 00/39164 | 7/2000 |
| WO | WO 01/68816 | 9/2001 |
| WO | WO 01/77172 | 10/2001 |
| WO | WO 03/004637 | 1/2003 |
| WO | WO 03/091282 | 11/2003 |

OTHER PUBLICATIONS

Adachi et al., "Cloning and Characterization of cDNA Encoding Human A-Type Endothelin Receptor", *Biochemical and Biophysical Research Communications*, 180:1265-1272, (1991).
Arrang et al., "Auto-inhibition of brain histamine release mediated by a novel class ($H_3$) of histamine receptor", *Nature*, 302(5911):832-7, (1983).
Bonner et al., "Cloning and Expression of the Human and Rat m5 Muscarnic Acetylcholine Receptor Genes", *Neuron*, 1:403-410, (1988).
Bruno et al., "Molecular Cloning and Sequencing of a cDNA Encoding a Human $α_{1A}$ Adrenergic Receptor", *Biochemical and Biophysical Research Communications*, 179:1485-1490, (1991).
Cherifi et al., "Purification of a Histamine H3 Receptor Negatively coupled to Phosphoinositide Turnover in the Human Gastric Cell Line HGT1", J Biol Chem, 267(35):25315-20, (1992).
M.F. Bonaldo, et al., EMBL Accesion No. AA859887, Mar. 14, 1998.
Frielle et al., "Cloning of the cDNA for the human $β_1$-adrenergic receptor", *Proc. Natl. Acad. Sci. USA*, 84:7920-7924, (1987).
L. Hillier, et al., GenBank Accession No. R87217, Oct. 10, 1995.
Jasper et al., "Primary structure of the mouse $β_1$ -Adrenergic receptor gene",*Biochemica et Biophysica Acta*, 1178:307-309, (1993).
Kakar et al., "Cloning, Sequencing, and Expression of Human Gonadotropin Releasing Hormone (GnRH) Receptor", *Biochemical and Biophysical Research Communications*, 189:289-295, (1992).
Laitinen et al., "Guanosine 5'-(γ-[35S]Thio)triphosphate Autoradiography Allows Selective Detection of Histamine H3 Receptor-Dependent G Protein Activation in Rat Brain Tissue Sections", J Neurochem, 71(2):808-16, (1998).
Larhammar et al., "Cloning and Functional Expression of a Human Neuropeptide Y/Peptide YY Receptor of the Y1 Type", *The Journal of Biological Chemistry*, 267:10935-10938, (1992).
Lee et al., "Cloning and expression of a cDNA encoding bovine muscarinic acetylcholine m3 receptor", *Biochimica et Biophysica Acta*, 1223:151-154, (1994).

(Continued)

*Primary Examiner*—John Ulm
(74) *Attorney, Agent, or Firm*—Fish & Richardson P.C.

(57) ABSTRACT

A full-length cDNA encoding a human-derived G protein-coupled receptor protein is isolated by screening a human hippocampus library. Also, a rat-derived cDNA corresponding to the human-derived cDNA is isolated. Proteins encoded by these cDNAs have an activity of lowering intracellular cAMP concentration under stimulation with histamine. These proteins are usable as tools in screening ligands thereof or in screening candidate compounds for drugs capable of regulating signal transduction from the above proteins.

16 Claims, 5 Drawing Sheets

OTHER PUBLICATIONS

Leurs et al., "Therapeutic potential of histamine H3 receptor agonists and antagonists", *Trends Pharmacol Sci*, 19(5):177-83, (1998).

Leurs et al., "The histamine H3-receptor: A target for developing new drugs," *Prog Drug Res* 39:127-65, (1992).

Libert et al., "Selective Amplification and Cloning of Four New Members of the G Protein-Coupled Receptor Family", *Science*, 244:569-572, (1989).

Link et al., "Cloning of Two Mouse Genes Encoding $\alpha_2$-Adrenergic Receptor Subtypes and Identification of a Single Amino Acid in the Mouse $\alpha_2$-C10 Homolog Responsible for an Interspecies Variation in Antagonist Binding", *Molecular Pharmacology*, 42:16-27, (1992).

Lovenberg et al., "Cloning and Functional Expression of the Human Histamine H3 Receptor", *Molecular Pharmacology* 55:1101-1107, (1999).

Mahan et al., "Expression of striatal $D_1$ dopamine receptors coupled to inositol phosphate production and $Ca^{2+}$ mobilization in *Xenopus* oocytes", *Proc. Natl. Acad. Sci. USA*, 87:2196-2200, (1990).

Masu et al., "Sequence and expression of a metabotropic glutamate receptor", *Nature*, 349:760-765, (1991).

Peralta et al., "Distinct primary structures, ligand-binding properties and tissue-specific expression of four human muscarinic acetylcholine receptors", *The EMBO Journal*, 6:3923-3929, (1987).

Regan et al., "Cloning and expression of a human kidney cDNA for an $\alpha_2$-adrenergic receptor subtype", *Proc. Natl. Acad. Sci. USA*, 85:6301-6305, (1988).

Ruat et al., "Reversible and irreversible labeling and autoradiographic localization of the cerebral histamine $H_2$ receptor using [$^{125}$I] iodinated probes", *Proc. Natl. Acad. Sci. USA*, 87:1658-1662, (1990).

Takayanagi et al., "Molecular Cloning, Sequence Analysis and Expression of a cDNA Encoding Human Type-1 Angiotensin II Receptor", *Biochemical and Biophysical Research Communications*, 183:910-916, (1992).

Yamada et al., "Cloning and functional characterization of a family of human and mouse somatostatin receptors expressed in brain, gastrointestinal tract, and kidney", *Proc. Natl. Acad. Sci. USA*, 89:251-255, (1992).

Arrang et al., "Highly potent and selective ligands for histamine $H_3$-receptors," *Nature*, 327:117-123 (1987).

Benjamin et al., "A plasticity window for blood vessel remodelling is defined by pericyte coverage of the preformed endothelial network and is regulated by PDGF-B and VEGF,"*Development*, 125:1591-1598 (1998).

Bork, "Powers and Pitfalls in Sequence Analysis: The 70% Hurdle," *Genome Res.*, 10:398-400 (2000).

Costa et al., "Drug Efficacy at Guanine Nucleotide-Binding Regulatory Protein-Linked Receptors: Thermodynamic Interpretation of Negative Antagonism and of Receptor Activity in the Absence of Ligand," *Mol. Pharmacol.*, 41:549-560 (1992).

Francesconi et al., "Role of the Second and Third Intracellular Loops of Metabotropic Glutamate Receptors in Mediating Dual Signal Transduction Activation," *J. Biol. Chem.*, 273:5615-5624 (1998).

Hasegawa et al., "Two Isoforms of the Prostaglandin E Receptor EP3 Subtype Different in Agonist-independent Constitutive Activity," *J. Biol. Chem.*, 271:1857-1869 (1996).

Kjelsberg et al., "Constitutive Activation of the $\alpha_{1B}$-Adrenergic Receptor by All Amino Acid Substitutions at a Single Site. Evidence for a Region which Constrains Receptor Activation," *J. Biol. Chem.*, 267:1430-1433 (1992).

Lameh et al., "Structure and Function of G Protein Coupled Receptors," *Pharm. Res.*, 7: 1213-1221 (1990).

Lefkowitz et al., "Constitutive activity of receptors coupled to guanine nucleotide regulatory proteins," *Trends Pharmacol. Sci.*, 14:303-307 (1993).

Ligneau et al., "Distinct pharmacology of rat and human histamine $H_3$ receptors: role of two amino acids in the third transmembrane domain," *Br. J. Pharmacol.*, 131:1247-1250 (2000).

Lovenberg et al., "Cloning of Rat Histamine $H_3$ Receptor Reveals Distinct Species Pharmacological Profiles," *J. Pharmacol. Exp. Ther.*, 293:771-778 (2000).

Milligan et al., "Inverse agonism: pharmacological curiosity of potential therapeutic strategy?" *Trends Pharmacol. Sci.*, 16:10-13 (1995).

Morisset et al., "High constitutive activity of native $H_3$ receptors regulates histamine neurons in brain," *Nature*, 408:860-864 (2000).

Onodera et al., "Possible roles of brain histamine H3 receptors and the pharmacology of its ligands," *Jpn. J. Psychopharmacol.*, 15:87-102 (1995) (English abstract included).

Rouleau et al., "Histamine $H_3$-receptor-mediated [$^{35}$S]GTP$\gamma$[S] binding: evidence for constitutive activity of the recombinant and native rat and human $H_3$ receptors," *Br. J. Pharmacol.*, 135:383-392 (2002).

Segal et al., "*Helicobacter pylori* attachment to gastric cells induce cytoskeletal arrangements and tyrosine phosphorylation of host cell proteins," *Proc. Natl. Acad. Sci. USA*, 93:1259-1264 (1996).

Skolnick et al., "From genes to protein structure and function: novel applications of computational approaches in the genomic era," *Trends Biotechnol.*, 18:34-39 (2000).

Tarvidel-Lacombe et al., "Cloning and cerebral expression of the guinea pig histamine $H_3$ receptor: evidence for two isoforms," *Neuroreport*, 11:755-759 (2000).

Wells, "Additivity of Mutational Effects in Proteins," *Biochemistry*, 29:8509-8517 (1990).

Wieland et al., "Constitutive Activity of Histamine $H_3$ Receptors Stably Expressed in SK-N-MC Cells: Display of Agonism and Inverse Agonism by $H_3$ Antagonists," *J. Pharmacol. Exp. Ther.*, 299:908-914 (2001).

Hillier et al., "The WashU-Merck EST Project", EMBL Id. No. R87217, Database Accession No. 946030 XP002196770, Oct. 10, 1995.

GUANOSINE TRIPHOSPHATE (GTP) BINDING PROTEIN-COUPLED RECEPTOR PROTEINS THAT BIND HISTAMINE AND ARE EXPRESSED IN THE BRAIN

This application is a divisional application of U.S. patent application Ser. No. 10/759,463, filed on Jan. 16, 2004, now U.S. Pat. No. 7,074,594 which is a divisional application of U.S. patent application Ser. No. 09/891,053, now U.S. Pat. No. 6,750,322, filed on Jun. 25, 2001, which is a continuation-in-part of PCT/JP99/07280, filed on Dec. 24, 1999, which claims priority from PCT/JP98/05967, filed on Dec. 25, 1998, and Japanese Application No. 11/145,661, filed on May 25, 1999.

TECHNICAL FIELD

The present invention relates to novel guanosine triphosphate binding protein-coupled receptor proteins, DNA encoding the proteins, and methods of screening for drug-candidate compounds using them.

BACKGROUND ART

Many hormones and neurotransmitters regulate physiological functions through specific receptor proteins located on the cell membrane. Many of these receptor-proteins transduce signals into the cell by activating a guanosine triphosphate binding protein (occasionally referred to as "G protein" below) that is coupled to them. These receptor proteins are thereby named as G protein-coupled receptors. Since they have a common structure, composed of seven transmembrane regions, they are also generally called "seven-transmembrane receptor proteins."

G protein-coupled receptors, which are expressed on the surface of cells in vivo and functioning cells of tissues, play an extremely important role as a target of molecules such as hormones, neurotransmitters, and biologically active compounds, which regulate the functions of these cells and tissues. Therefore, G protein-coupled receptor proteins have received great attention as targets in drug-development.

G protein-coupled receptors reported so far include: muscarinic acetylcholine receptors M1, M2, M3, and M4 (Peralta et al., EMBO J., 6:3923-3929 (1987)), muscarinic acetylcholine receptor M5 (Bonner et al., Neuron, 1:403-410 (1988)), adenosine receptor A1 (Libert et al., Science, 244: 569-572 (1989)), α1A adrenoreceptor (Bruno et al., Biochem. Biophys. Res. Commun., 179:1485-1490 (1991)), β1 adrenoreceptor (Frielle et al., Proc. Natl. Acad. Sci. USA, 84:7920-7924 (1987)), angiotensin receptor $AT_1$ (Takayanagi et al., Biochem. Biophys. Res. Commun., 183:910-916 (1992)), endothelin receptor ETA (Adachi et al., Biochem. Biophys. Res. Commun., 180:1265-1272 (1991)), gonadotropin releasing factor receptor (Kaker et al., Biochem. Biophys. Res. Commun., 189:289-295 (1992)), histamine receptor $H_2$ (Ruat et al., Proc. Natl. Acad. Sci. USA, 87:1658-1672 (1992)), neuropeptide Y receptor Y1 (Larhammar et al., J. Biol. Chem., 267:10935-10938 (1992)), interleukin-8 receptor IL8RA (Holmes et al., Science, 2563: 1278-1280 (1991)), dopamine receptor $D_1$ (Mahan et al., Proc. Natl. Acad. Sci. USA, 87:2196-2200 (1990)), metabolic glutamate receptor mGluR1 (Masu et al., Nature, 349:760-765 (1991)), and somatostatin receptor $SS_1$ (Yamada et al., Proc. Natl. Acad. Sci. USA, 89:251-255) (for reference, Watson S. and Arkinstall S., The G protein Linked Receptor FactsBook, Academic Press (1994)). Examples of developed medicines aimed at G protein-coupled receptors are: terazosine hydrochloride (antihypertensive agent, α1 adrenoreceptor antagonist), atenolol (antiarrhythmia, β1 adrenoreceptor antagonist), dicyclomine hydrochloride (antispasmodic agent, acetylcholine receptor antagonist), ranitidine hydrochloride (drug for peptic ulcers, histamine receptor H2 antagonist), trazodone hydrochloride (antidepressant, serotonin receptor 5-HT1B antagonist), and buprenorphine hydrochloride (analgesic agent, opioid receptor κ agonist) (for reference, Stadel et al., Trends Pharm. Sci., 18:430-437 (1997); Medicine Handbook $5^{th}$ edition, Yakugyo-Jiho).

The hypothalamus, a part of the brain which governs a number of programs that trigger a particular response, contributes to the homeostasis of the internal environment by means of a variety of outputs, as the center of the autonomic nervous system. For instance, it releases hormones such as thyrotropic hormone-releasing hormone, gonadotropic hormone-releasing hormone, and growth hormone-releasing hormone, and thereby regulates the entire endocrine system through the actions of these hormones on the specific receptors expressed in target cells. These outputs in the hypothalamus are thought to be mediated by receptors expressed in the hypothalamus and compounds reacting with them. Therefore, elucidation of the relationship between the compounds regulating the hypothalamus outputs and their specific receptors expressed in the hypothalamus is extremely important in developing novel medicines for the treatment of diseases arising from endocrine disorders.

DISCLOSURE OF THE INVENTION

The present invention provides a novel human-derived G protein-coupled receptor protein and rat-derived one corresponding thereto, both of which are expressed in the brain (in particular, thalamus and hypothalamus, etc.). It also provides a method of screening for ligands and drug-candidate compounds using these receptor proteins.

The inventors first selected a region highly conserved in known G protein-coupled receptor proteins, then designed primers corresponding to the region, and performed reverse transcriptase-polymerase chain reaction (RT-PCR) using mRNA obtained from rat thalamus and hypothalamus. Next, amplified clones were randomly selected, and their partial nucleotide sequences were determined. To remove known clones from the nucleotide sequence determined-clones, colony-hybridization was performed using, as a probe, cDNA clones judged by homology search to be encoding a known G protein-coupled receptor protein. Negative clones that failed to hybridize with any probe were selected. Using probes prepared based on the nucleotide sequence of the negative clones, the inventors screened cDNA libraries from rat thalamus and hypothalamus, and succeeded in isolating a full-length cDNA (rat BG2 cDNA) encoding a rat G protein-coupled receptor.

Moreover, the present inventors screened human hippocampus libraries using specific probes and successfully isolated a human cDNA (human BG2 cDNA) corresponding to the rat cDNA.

To identify a ligand for the G protein-coupled receptor protein encoded by the isolated human BG2 cDNA, the present inventors prepared cells expressing the protein and stimulated the protein to screen compounds which changed the concentration of cAMP in the cells. As a result, histamine was found to have an activity of stimulating the human G protein-coupled receptor protein expressed on the cell surface and lowering the intracellular cAMP concentration.

In addition, histamine was found to have an activity of actually binding to the protein.

The present inventors also isolated a cDNA encoding an alternative splicing variant for rat BG2 (rat BG2-2 cDNA), expressed the protein encoded by the cDNA on a cell surface, and detected the response against the histamine stimulation, to find that the protein had an activity of reducing the intracellular cAMP concentration in response to the histamine stimulation in the same manner as in human BG2.

The G protein-coupled receptor protein found by the present inventors is a very useful tool in screening for agonists and antagonists thereof, and the agonists and antagonists isolated by the screening are expected to be used as pharmaceuticals.

The present invention relates to novel human- and rat-derived G protein-coupled receptor proteins, DNAs encoding them, and screening of ligands and drug-candidate compounds using the proteins.

Specifically, the invention relates to:

(1) a guanosine triphosphate-binding protein-coupled receptor protein comprising the amino acid sequence selected from the group consisting of:

(a) the amino acid sequence of SEQ ID NO:20 or 25, and (b) the amino acid sequence of SEQ ID NO:20 or 25, in which one or more amino acids are replaced, deleted, or added;

(2) the protein of (1), wherein the protein has an activity of binding to histamine;

(3) the protein of (1), wherein the protein has an activity of changing the intracellular cAMP concentration or calcium concentration in response to histamine stimulation;

(4) a partial peptide of the receptor protein of any one of (1) to (3);

(5) a DNA encoding the receptor protein of any one of (1) to (3) or the partial peptide of (4);

(6) the DNA of (5), wherein the DNA comprises a coding region of the nucleotide sequence of SEQ ID NO:21 or 26;

(7) a vector containing the DNA of (5) or (6);

(8) a transformant carrying the DNA of (5) or (6) or the vector of (7);

(9) a method for producing the receptor protein of any one of (1) to (3) or the partial peptide of (4), the method comprising the steps of culturing the transformant of (8) and recovering the protein or peptide from the transformant or its culture supernatant;

(10) a method of screening for a ligand which binds to the receptor protein of any one of (1) to (3), or an analogue thereof, the method comprising the steps of:

(a) exposing a test compound to the receptor protein of any one of (1) to (3) or the partial peptide of (4), and (b) selecting the compound that binds to the protein or partial peptide;

(11) a method of screening for a compound that inhibits the binding between the receptor protein of any one of (1) to (3) and its ligand or an analogue of the ligand, the method comprising the steps of:

(a) exposing a ligand or its analogue to the receptor protein of any one of (1) to (3) or the partial peptide of (4) in the presence of a test compound, and detecting the binding activity between the protein or partial peptide and the ligand or its analogue, and (b) comparing the binding activity detected in (a) with that in the absence of the test compound, and selecting the compound that reduces the binding activity;

(12) the method of (11), wherein the ligand is histamine;

(13) a method of screening for a compound which inhibits or promotes the activity of the receptor protein of any one of (1) to (3), the method comprising the steps of:

(a) exposing a ligand for the protein or an analogue thereof to cells expressing the protein in the presence of a test compound, (b) detecting a change in cells associated with the binding of the protein to the ligand or the analogue thereof, and (c) selecting a compound which inhibits or promotes the change in the cells detected in (b) in comparison with the change in the cells in the absence of the test compound;

(14) the method of (13), wherein the ligand is histamine;

(15) the method of (13) or (14), wherein the change in cells to be detected is selected from the group consisting of a change in cAMP concentration, a change in calcium concentration, an activation of G protein, an activation of phospholipase C, and a change in pH;

(16) a kit for the method of any one of (10) to (15), the kit comprising the receptor protein of any one of (1) to (3) or the partial peptide of (4);

(17) an antibody which binds to the receptor protein of any one of (1) to (3);

(18) a compound isolated by the method of any one of (11) to (15); and

(19) a pharmaceutical composition comprising the compound of (18) as an active ingredient.

"G protein-coupled receptor protein" herein refers to a receptor protein that transduces intracellular signals by activating G proteins.

"Ligand" refers to a natural compound capable of binding to a G protein-coupled receptor and inducing signal transduction. "Analogue of a ligand" herein refers to a derivative of the ligand having the same physiological activity as the ligand binding to a G protein-coupled receptor protein, or inhibiting a physiological activity of the ligand, and contains both natural and artificially synthesized compounds. For example, histamine and R(−)-α-methylhistamine correspond to a ligand and an analogue thereof, respectively.

"Agonist" refers to a compound having a bioactivity similar to that of the ligands of G protein-coupled receptors, including both natural and artificially synthesized compounds.

"Antagonist" refers to a compound capable of inhibiting the bioactivity of a ligand of a G protein-coupled receptor, including both natural and artificially synthesized compounds.

"Protein" and "peptide" as used herein include their salts as well.

An "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different DNA molecules, transfected cells, or cell clones, e.g., as these occur in a DNA library such as a cDNA or genomic DNA library.

The term "substantially pure" as used herein in reference to a given polypeptide means that the polypeptide is substantially free from other biological macromolecules. For example, the substantially pure polypeptide is at least 75%, 80, 85, 95, or 99%) pure by dry weight. Purity can be measured by any appropriate standard method known in the art, for example, by column chromatography, polyacrylamide gel electrophoresis, or HPLC analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The present invention provides novel G protein-coupled receptor proteins derived from human and rat. The nucleotide sequence of the cDNA encoding human G protein-coupled receptor (human BG2) isolated herein is shown in SEQ ID NO:21, and the amino acid sequence of the human BG2 protein is shown in SEQ ID NO:20. The nucleotide sequence of the cDNA encoding rat G protein-coupled receptor (rat BG2-2) isolated in the present invention is shown in SEQ ID NO:26, and the amino acid sequence of the rat BG2-2 protein is shown in SEQ ID NO:25.

Human BG2 protein has 32%, 28%, and 27% homology to known G protein-coupled receptors, namely human α-2C-1 adrenoreceptor (Regan et al., Proc. Natl. Acad. Sci. USA, 85:6301-6305 (1988)), mouse β-1 adrenoreceptor (Jasper et al., Biochim. Biophys. Acta., 1178:307-309 (1993)), and human muscarinic acetylcholine receptor M3 protein (Peralta et al., EMBO J., 6:3923-3929 (1987)), respectively. These results suggest that the human BG2 proteins belong to the G protein-coupled receptor family. Furthermore, this suggests that they participate in signal transduction through the activation of G proteins upon ligand binding. In fact, human BG2 protein has an activity of binding to histamine, and of reducing the intracellular cAMP concentration in response to the stimulation by histamine. Human BG2 protein of the present invention was expressed in the brain (for example, hippocampus). In brain, hippocampus plays an important role in memory and learning, the cerebellum regulates the body motions, and the hypothalamus serves as the center of the autonomic nervous system. Thus, the human BG2 proteins are assumed to be involved in the regulation of these functions. Therefore, the proteins and genes, or an agonist or antagonist that can regulate the human BG2 protein function(s), can be used in the treatment of disabilities in memory and learning, or the control of the autonomous nervous system, such as regulation of blood pressure, digestion, body temperature, food-intake, etc. In addition, rat BG2-2 protein is a rat protein corresponding to human BG2 protein and is, like human BG2 protein, a G protein-coupled receptor protein whose ligand is histamine.

The proteins of the present invention may be prepared as natural proteins, and also as recombinant proteins, by using recombinant DNA technology. A natural protein may be prepared, for instance, by extracting tissues, speculated to express the protein of the present invention, and performing immunoaffinity chromatography using antibody as described later on. On the other hand, a recombinant protein can be prepared by culturing transformant cells carrying DNA encoding the protein of the present invention as described later on. One skilled in the art can prepare an altered protein having a function or an activity (transduction of intracellular signals through G protein activation, binding activity to histamine, and activity of varying concentration of intracellular cAMP or calcium responded by histamine stimulation) equivalent to that of the natural protein by introducing modifications such as replacement of any amino acid contained in the natural protein of the present invention (SEQ ID NO:20 or SEQ ID NO:25) according to known methods. Mutations of amino acids in a protein may occur naturally. The G protein-coupled receptor proteins of the present invention include such mutant proteins having an amino acid sequence altered by replacement, deletion or addition, having a function equivalent to that of the natural protein. The methods of altering amino acids, known to one skilled in the art, include, the Kunkel method (Kunkel et al., Methods Enzymol., 154:367-382 (1987)), double primer method (Zoller et al., Methods Enzymol., 154:329-350 (1987)), cassette mutation (Wells et al., Gene, 34:315-323 (1985)), and megaprimer method (Sarkar et al., Biotechniques, 8:404-407 (1990)). The number of mutated amino acids in a functionally equivalent protein is generally not more than 10% of all the amino acids, preferably not more than 10 amino acids, and more preferably not more than 3 amino acids (for instance, one amino acid).

The invention also includes a polypeptide, or fragment thereof, that differs from the corresponding sequence shown as SEQ ID NO:20 or SEQ ID NO:25. The differences are, preferably, differences or changes at a non-essential residue or a conservative substitution. In one embodiment, the polypeptide includes an amino acid sequence at least about 60% identical to a sequence shown as SEQ ID NO:20 or SEQ ID NO:25, or a fragment thereof. Preferably, the polypeptide is at least 65%, 70%, 75%, 80%, 85%, 90%, 95%, 98%, 99% or more identical to SEQ ID NO:20 or SEQ ID NO:25 and has at least one G-protein coupled receptor protein function or activity described herein. Preferred polypeptide fragments of the invention are at least 10%, preferably at least 20%, 30%, 40%, 50%, 60%, 70%, or more, of the length of the sequence shown as SEQ ID NO:20 or SEQ ID NO:25 and have at least one G-protein coupled receptor protein activity described herein. Or alternatively, the fragment can be merely an immunogenic fragment.

As used herein, "% identity" of two amino acid sequences, or of two nucleic acid sequences, is determined using the algorithm of Karlin and Altschul (PNAS USA, 87:2264-2268, 1990), modified as in Karlin and Altschul, PNAS USA, 90:5873-5877, 1993). Such an algorithm is incorporated into the NBLAST and XBLAST programs of Altschul et al. (J. Mol. Biol., 215:403-410, 1990). BLAST nucleotide searches are performed with the NBLAST program, score=100, wordlength=12. BLAST protein searches are performed with the XBLAST program, score=50, wordlength=3. To obtain gapped alignment for comparison purposes GappedBLAST is utilized as described in Altschul et al. (Nucleic Acids Res., 25:3389-3402, 1997). When utilizing BLAST and GappedBLAST programs the default parameters of the respective programs (e.g., XBLAST and NBLAST) are used to obtain nucleotide sequences homologous to a nucleic acid molecule of the invention.

The present invention also includes partial peptides of the above-described G protein-coupled receptor proteins. The partial peptides of the present invention include, for instance, those corresponding to the N-terminal region of the G protein-coupled receptor protein, which can be utilized to prepare an antibody. Moreover, partial peptides of the present invention include peptides having the binding activity to histamine and peptides having an activity of changing the intracellular cAMP concentration or calcium concentration in response to the stimulation by histamine when expressed on the cell surface. These peptides can be used for screening drug-candidate compounds as described below. Moreover, a partial peptide which has the binding activity to histamine but does not have an activity of conducting the signal transduction into cells, can be a competitive inhibitor for the proteins of the present invention. Such partial peptides of the invention usually have a length of at least 15 amino acids, and preferably 20 amino acids or more.

Furthermore, the present invention provides DNA encoding the proteins of the invention as described above or partial peptides thereof. The DNA encoding the protein of the invention or partial peptide thereof include cDNA, genomic DNA, and synthetic DNA, but are not so limited as long as they encode the proteins or the peptides. cDNA encoding the proteins of the present invention can be screened by labeling, with $^{32}P$ or the like, for example, the cDNA as described in SEQ ID NO:21 or NO:26, a part of it, complementary RNA to the DNA, or a synthetic oligonucleotide comprising a part of the cDNA and by hybridizing them to a cDNA library from a tissue expressing the protein of the present invention (for instance, brain tissue). Alternatively, cDNA may be cloned by synthesizing an oligonucleotide corresponding to the nucleotide sequence of the cDNA, and amplifying cDNA from an appropriate tissue (such as brain tissue) by PCR. Genomic DNA can be obtained by screening a genomic library by hybridization using, as a $^{32}P$-labeled probe, the cDNA as described in SEQ ID NO:21 or NO:26, or a part of it, complementary RNA to the DNA, or a synthetic oligonucleotide comprising a part of the cDNA. Alternatively, it may be cloned by synthesizing an oligonucleotide corresponding to the nucleotide sequence of the cDNA, and amplifying genomic DNA by PCR. Synthetic DNA can be prepared by chemically synthesizing oligonucleotides comprising a part of the nucleotide sequence of SEQ ID NO:21 or NO:26, annealing them into a double strand, and ligating them using DNA ligase (Khorana et al., J. Biol. Chem., 251:565-570 (1976); Goeddel et al., Proc. Natl. Acad. Sci. USA, 76:106-110 (1979)).

In one aspect, the invention provides an isolated or purified nucleic acid molecule that encodes a polypeptide described herein or a fragment thereof. Preferably, the isolated nucleic acid molecule includes a nucleotide sequence that is at least 60% identical to the nucleotide sequence shown in SEQ ID NO:21 or SEQ ID NO:26. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:21 or SEQ ID NO:26. In the case of an isolated nucleic acid molecule which is longer than or equivalent in length to the reference sequence, e.g., SEQ ID NO:21 or SEQ ID NO:26, the comparison is made with the full length of the reference sequence. Where the isolated nucleic acid molecule is shorter that the reference sequence, e.g., shorter than SEQ ID NO:21 or SEQ ID NO:26, the comparison is made to a segment of the reference sequence of the same length (excluding any loop required by the homology calculation).

The invention also includes nucleic acid sequences that hybridize to the nucleic acid molecule shown as SEQ ID NO:21 or SEQ ID NO:26, or a fragment thereof. Hybridization is performed in 6×SSC, 40% formamide at 25° C., followed by a wash in 1×SSC at 55° C. (low stringency); in 6×SSC, 40% formamide at 37° C., followed by a wash in 0.2×SSC at 55° C. (medium stringency); or in 6×SSC, 40% formamide at 37° C., followed by a wash in 0.1×SSC at 62° C. (high stringency).

These DNA can be used for producing recombinant proteins. Namely, it is possible to prepare the protein of the invention as a recombinant protein by inserting a DNA encoding the receptor protein (DNA as described in SEQ ID NO:21 or NO:26, for instance) into an appropriate expression vector, culturing a transformant obtained by introducing the vector into an appropriate cell, and purifying the expressed protein. Since the protein of the invention is a receptor protein, it is possible to prepare it in a form expressed on the cell membrane.

Specifically, if the host is *Escherichia coli*, the plasmid vectors such as pET-3 (Rosenburg et al., Gene, 56:125-135 (1987)) and pGEX-1 (Smith et al., Gene, 67:31-40 (1988)) may be used. *E. coli* can be transformed by the Hanahan method (Hanahan D., J. Mol. Biol., 166:557-580 (1983)), electroporation (Dower et al., Nucleic Acids Res., 16:6127-6145 (1988)), and such. If the host is fission yeast (*Schizosaccharomyces pombe*), a plasmid vector such as pESP-1 (Lu et al., Gene, 200:135-144 (1997)) may be used. Yeast can be transformed by spheroplast fusion (Beach et al., Nature, 290:140 (1981)), lithium acetate method (Okazaki et al., Nucleic Acids Res., 18:6485-6489 (1990)), etc.

If the host is a mammalian cell, such as Chinese Hamster ovary-derived (CHO) cells and human HeLa cells, vectors such as pMSG (Clontech) may be used. Recombinant DNA may be introduced into mammalian cells by calcium phosphate method (Graham et al., Virology, 52:456-467 (1973)), DEAE-dextran method (Sussman et al., Mol. Cell. Biol., 4:1641-1643 (1984)), lipofection (Felgner et al., Proc. Natl. Acad. Sci. USA, 84:7413-7417 (1987)), electroporation (Neumann et al., EMBO J., 1:841-845 (1982)), etc. If the host is an insect cell, a baculovirus vector such as pBac-PAK8/9 (Clontech) can be used. Transformation of insect cells is done by the methods described in the literature (Bio/Technology 6:47-55 (1980)).

Recombinant proteins expressed in host cells can be purified by known methods. The proteins can also be synthesized as fusion proteins tagged with histidine residues at the N-terminus, or fused to glutathione-S-transferase (GST), and purified by using their binding ability toward a metal chelating resin, or a GST affinity resin (Smith et al., J. Biol. Chem., 263:7211-7215 (1988)), respectively. For instance, when the vector pESP-1 is used, the protein of interest is synthesized as a fusion protein with GST, which can be purified using GST affinity resin. The fusion protein may be digested with thrombin, or blood coagulating factor Xa to liberate the protein of interest.

Moreover, DNA encoding the proteins of the present invention can be used in gene therapy of diseases that arise from a mutation of the protein. When used in gene therapy, the DNA can be introduced into human cells using retrovirus vectors (Danos et al., Proc. Natl. Acad. Sci. USA, 85:6460-6464 (1988); Dranoff et al., Proc. Natl. Acad. Sci. USA, 90:3539-3543 (1993)), adenovirus vectors (Wickham et al., Cell, 73:309-319 (1993)), etc. To administer the vector to patients, transplantation of bone marrow, subcutaneous injection, and intravenous injection can be used (Asano S., Protein Nucleic acid and Enzyme, 40:2491-2495 (1995)).

Furthermore, the present invention provides antibodies capable of binding to the proteins of the invention. Antibodies against the proteins can be prepared by known methods in the art (for instance, refer to Shin-Seikagaku-Jikken-Kouza I: Protein I 389-406, Tokyo-Kagaku-Doujin). For instance, polyclonal antibodies are prepared as follows. An appropriate dose of the above proteins or partial peptides thereof are administered into immune animals such as rabbits, guinea pigs, mice, or chickens. Administration may be performed together with an adjuvant (such as FIA or FCA) that promotes antibody production, and usually performed every couple of weeks. The titer of antibodies can be increased by performing multiple immunizations. After the final immunization, antisera are obtained by withdrawing blood from immune animals. Polyclonal antibodies are purified from antisera by ammonium sulfate precipitation, fractionation by anion exchange chromatography, or affinity chromatography with either Protein A or immobilized antigen. Monoclonal antibodies are prepared as follows. The proteins of the invention or partial peptides thereof are administered into immune animals as described above. After the final immunization, their spleens or lymph nodes are excised. Then, antigen-producing cells are recovered from the spleens or the lymph nodes, and fused with myeloma cells using polyethylene glycol and such to produce hybridomas. Desired hybridomas are selected by screening, and their culture supernatant is used to prepare monoclonal antibodies. Monoclonal antibodies can be purified by ammonium sulfate precipitation, fractionation by anion exchange chromatography, or affinity chromatography with either Protein A or immobilized antigen. Antibodies prepared thereby can be used not only in affinity purification of the protein of the invention, but also for the diagnosis or antibody treatment of diseases arising from the abnormal expression of the receptors, or detection of the expression level of the receptors.

If used for antibody treatment, humanized antibodies or human antibodies are preferable. Humanized antibodies, in case of mouse-human chimeric antibodies, are prepared by isolating the gene encoding the antibody against the G protein-coupled receptor protein from the producing mouse cells, replacing the constant region of the H chain of the antibody with that of the human IgE, and introducing it into mouse myeloma J558L cells (Neuberger et al., Nature, 314:268-270 (1985)). Human antibodies can be prepared by immunizing mice, whose immune system is replaced with that of human, with the protein.

Furthermore, the present invention provides a method of screening for ligands or their analogues of the protein of the invention. The methods include such processes as exposing a test compound to the G protein-coupled receptor protein or its partial peptide, and selecting compounds that are capable of binding to the proteins or the peptide. Compounds to be tested include compounds or their analogues such as acetylcholine, adenosine, adrenaline, noradrenaline, angiotensin, bombesin, bradykinin, C5a anaphylatoxin, calcitonin, cannabinoids, chemokines, cholecystokinin, dopamine, endothelin, formylmethionylpeptide, GABA, galanin, glucagon, glutamate, glycopeptide hormone, histamine, 5-hydroxytryptophan, leucotriene, melanocortin, neuropeptide Y, neurotensin, odorant, opioid peptide, opsin, parathyroid hormone, platelet activating factor, prostanoid, somatostatin, tachykinin, thrombin, thyrotropin releasing hormone, vasopressin, and oxytocin (Watson S. and Arkinstall S., G protein Linked Receptor FactsBook, Academic Press (1994)), and also other purified proteins, expressed products of genes (including libraries), extracts of tissues or cells in which the ligand is stipulated to be expressed (the brain, thalamus, and hypothalamus etc.), and the culture medium of the cells. The proteins may be used in a form expressed in desired cells (including transformants genetically engineered to express the proteins) or on the cell surface, in the form of the membrane fractions of the cells, or in a form bound to an affinity column. If necessary, test compounds may be labeled appropriately. Methods for labeling include radioisotope labeling, and fluorescence labeling, but are not limited thereto. The binding between the proteins and test compounds can be examined by detecting the label added to the compound (for instance, measuring the radioactivity or fluorescence intensity), or using as an index, intracellular signaling triggered by the compound binding to the protein (such as G protein activation, the change in the concentration of $Ca^{2+}$ or cAMP, phospholipase C activation, and the change in pH). Specific methods can be employed as described in the literatures (Cell Calcium, 14:663-671 (1993); Analytical Biochemistry, 226:349-354 (1995); J. Biol. Chem., 268:5957-5964 (1993); Cell, 92:573-585 (1998); Nature, 393:272-273 (1998)), and unexamined published Japanese patent application (JP-A) No. Hei 9-268. Alternatively, the binding may be detected by measuring the activity of a reporter gene using two-hybrid system (Zervos et al., Cell, 72:223-232 (1994); Fritz et al., Nature, 376:530-533 (1995)).

The present invention also provides a method of screening for a compound which can inhibit the binding between the proteins of the invention and their ligands or their analogues. The method includes the steps of (a) exposing the ligand or its analogue to the proteins of the present invention or their partial peptides in the presence of a test compound, and detecting the binding activity between the proteins or partial peptides and the ligand or its analogue, and (b) comparing the binding activity detected in (a) with that in the absence of the test compound, and selecting a compound that reduces the binding activity. Compounds to be tested include proteins, peptides, non-peptide compounds, artificially synthesized compounds, extracts of tissues and cells, sera, but are not limited thereto. The proteins may be used in a form expressed in desired cells (including transformants genetically engineered to express the proteins) or on the cell surface, in a form of the membrane fractions of the cells, or in a form bound to an affinity column. If necessary, ligands may be labeled appropriately. Methods for labeling include radioisotope labeling, and fluorescence labeling, but are not limited thereto. As a ligand, for example, histamine can be preferably used. An analogue of histamine, for example, R(-)-α—methylhistamine, can be used.

The binding activity between the proteins of the present invention or their partial peptides and ligands or their analogues can be examined by detecting a label added to the ligand or its analogue (for instance, measuring the radioactivity or fluorescence intensity), or using cellular change, as an index, that are triggered by the compound binding to the protein (such as G protein activation, the change in the concentration of $Ca^{2+}$ or cAMP, phospholipase C activation, and the change in pH). Specific methods can be employed by the method of Zlokarmik et al. (Science, 1998, 279:84) as described in examples. Moreover, the methods can be employed as described in the literatures (Cell Calcium, 14:663-671 (1993); Analytical Biochemistry, 226:349-354 (1995); J. Biol. Chem., 268:5957-5964 (1993); Cell, 92:573-585 (1998); Nature, 393:272-273 (1998)), and JP-A No. Hei 9-268. If the results of the detection show that the binding activity in the presence of a test compound is lower than that in the absence of the compound (control), the compound is judged to be capable of inhibiting the binding between the proteins or their partial peptides and the ligands or their analogues. These compounds include those capable of triggering the intracellular signaling through binding to the protein (agonist), and those not having such activity (antagonist). Agonists have similar bioactivities to those of the ligands of the proteins. On the other hand, antagonists inhibit the bioactivities of the ligands. Therefore, these agonists and antagonists are useful as medicinal compositions for treatment of diseases arising from disorders in the signaling pathway mediated by the proteins.

In addition, the present invention provides a method of screening for a compound which inhibits or promotes an activity of the protein of the present invention. The screening method contains the steps of (a) exposing a ligand for the protein or an analogue thereof to cells expressing the protein in the presence of a test compound, (b) detecting a change in cells associated with the binding of the protein to the ligand or the analogue thereof, and (c) selecting a compound which inhibits or promotes the change in the cells detected in (b) in comparison with the change in the cells in the absence of the test compound. Compounds to be tested include proteins, peptides, non-peptide compounds, artificially synthesized compounds, extracts of tissues and cells, and sera, but are not limited thereto. A compound isolated by the screening in which the inhibition of the above binding activity is an index can be used as a test compound. Cells which express the proteins of the present invention can be prepared by, for example, inserting a DNA encoding the proteins to an appropriate vector, and introducing the vector into an appropriate animal cell, as described in Example 5. Into the expression vector, a marker gene for selecting a recombinant may be inserted. As a ligand for stimulating the proteins of the present invention, for example, histamine can be preferably used. An analogue of histamine, for example, R(−)-α-methylhistamine, can be used.

A change in cells associated with the binding of a ligand or an analogue thereof to the proteins of the present invention can be detected, for example, using, as an index, an activation of G protein, a concentration change of $Ca^{2+}$ or cAMP, an activation of phospholipase C, a change of pH. Specific methods can be employed by the method of Zlokarmik et al. (Science, 1998, 279:84) as described in Example 6. Moreover, the methods can be employed as described in the literatures (Cell Calcium, 14:663-671 (1993); Analytical Biochemistry, 226:349-354 (1995); J. Biol. Chem., 268:5957-5964 (1993); Cell, 92:573-585 (1998); Nature, 393:272-273 (1998)), and JP-A No. Hei 9-268).

As a result of this detection, when a test compound used inhibits a change in cells in comparison with that in cells in case of reacting a ligand or an analogue thereof in the absence of the test compound, the used test compound is judged to be a compound which inhibits an activity of the proteins of the present invention. In contrast, when a test compound enhances a change in the cells, the compound is judged to be a compound which promotes an activity of the protein of the present invention.

A compound isolated by the screening method of the present invention (an agonist or antagonist of the proteins of the present invention) can be applied to, for example, attention deficit hyperactivity disorder, Alzheimer's disease, memory disorder, dysgnosia, schizophrenia, sleep disorder, insomnia, sleep-induced apnea syndrome, narcolepsy, articular rheumatism, osteoarthritis, gastric ulcer, inflammatory intestine disorder, ischemic heart disease, arrhythmia, high or low blood pressure disorder, epilepsy, obesity, cibophobia, depression, anxiety, migraine, asthma, Huntington's disease, pain, nicotine abstinence symptoms (Trends in Pharmacological Science, 19:177-183; Stark et al., Drugs of the Future 21:507-520 (1996); Onodera et al., Jpn J. Psychopharmacol., 15:87-102 (1995)). When using these compounds as a drug, the isolated compound itself can be directly administered to the patient, or it can be given after formulating as pharmaceutical compositions by using commonly known pharmaceutical preparation methods. The compound may be administered after formulating by mixing with, for example, pharmaceutically acceptable carriers or media, and specifically, sterilized water, physiological saline, plant oils, emulsifiers, suspending agents, surfactants, stabilizers, binders, lubricants, sweeteners, flavors, coloring agents, and so on. The administration to patients is done by methods commonly known to those skilled in the art, such as intraarterial, intravenous, or subcutaneous injections and, in addition, intranasal, bronchial, intramuscular, or oral administrations. One skilled in the art can suitably select the dosage according to the body-weight or age of a patient, or the method of administration.

Furthermore, the present invention provides a kit for the screening described above, comprising the proteins of the present invention or their partial peptides. The proteins or their partial peptides may be in a form expressed in desired cells (including transformants genetically engineered to express the protein) or on the cell surface, in a form of membrane fractions of the cell, or in a form bound to an affinity column. Components of the kit of the invention may include, other than the above-described receptor protein samples, ligand samples (both labeled and unlabeled), and buffers for the reaction between the ligand and the receptor protein, and wash solutions. Labels to be added to the ligands include radioisotope and fluorescence, for instance. The kit of the invention can be used as described in JP-A No. Hei 9-268. Moreover, for example, in the screenings using the detection system of the cAMP concentration change described in Example 6, and the detection system of the binding activity described in Example 7, the kit of the present invention can be used.

All references and patents cited herein are incorporated by reference in their entirety.

DETAILED DESCRIPTION

Figure 1:
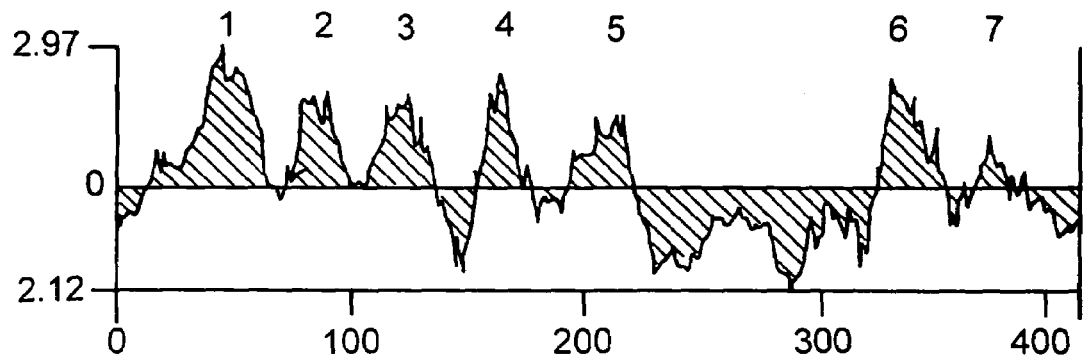
FIG. 1 shows the hydrophobicity plot of the rat BG2 protein. The seven hydrophobic regions (transmembrane regions) that are characteristics of the G protein-coupled receptor proteins are indicated by the numbers from 1 to 7. The numbers in the bottom indicate those of the amino acid residues in the BG2 protein.

The present invention is illustrated in detail below with reference to examples, but is not to be construed as being limited thereto.

EXAMPLE 1

Isolation of a Gene Encoding a Rat G Protein-Coupled Receptor

The G protein-coupled receptors share a characteristic structure composed of seven transmembrane regions, and the amino acid sequences of the transmembrane regions and the adjacent regions are well conserved. The present inventors first compared the nucleotide sequences of the second and the seventh transmembrane domains, which are highly conserved, with known G protein-coupled receptors: mouse neuropeptide Y receptor Y1 (GenBank Accession Number Z18280), rat Y1 (Z11504), human Y1 (M84755), mouse neuropeptide Y receptor Y4 (U40189), rat Y4 (Z68180), human Y4 (Z66526), and mouse neuropeptide Y receptor Y6 (U58367), and synthesized novel sense and antisense primers, as described in SEQ ID NO:3 and NO:4, respectively.

Next, single stranded cDNA was synthesized from poly (A)$^+$RNA prepared from rat (*Rattus norvegicus*) thalamus and hypothalamus using the RNA-PCR kit (TaKaRa), and PCR was performed using the two primers. Specifically, poly(A)$^+$RNA was purified from rat thalamus and hypothalamus using Fasttrack 2.0 kit (Invitrogen). Then, 75 ng of the poly(A)$^+$RNA was used to synthesize complementary DNA according to the protocol accompanying the RNA-PCR kit (TaKaRa). PCR amplification was performed using all the cDNA. The reaction mixture comprising each 0.15 mM dNTPs, 1.5 mM $MgCl_2$, 0.025 U/μl rTaq polymerase (TaKaRa), each of 0.5 μM degenerated primer Fg (SEQ ID NO:3) and Rb (SEQ ID NO:4), and 10×PCR buffer accompanying the enzyme was prepared making a total of 130 μl, and aliquoted into six 20-μl fractions. PCR was performed with the Pertier thermal cycler PTC200 (MJ Research) under conditions as follows: a single cycle of 94° C. for 2 min, followed by 35 cycles of 94° C. for 30 sec, 48° C. for 1 min, 72° C. for 1 min 30 sec, and then a single cycle of 72° C. for 8 min. After PCR, the six reaction-solutions were combined, and the amplified products were purified using the Wizard PCR purification kit (Promega), and then eluted with 30 μl of TE. 2 μl of the TE eluate was used for cloning into the pCR2.1 vector of the TOPO TA cloning kit (Invitrogen). XL1-Blue cells were used as the host cell and transformed using the *E. coli* pulser (BioRad). From the resulting transformants, 5,760 colonies having white or light blue color were randomly selected using the gene library construction system BioPick (BioRobotics), and inoculated into fifteen 384-well plates containing LB media supplemented with 100 μl ampicillin. Clones were cultured at 37° C. overnight, and replica plated onto a filter on top of a LB agar plate containing 100 μg/ml ampicillin and 25% glycerol, and another filter on top of a LB agar plate containing 100 μg/ml ampicillin, for preparing a glycerol stock, and colony hybridization, respectively, using a gene library replicating system BioGrid (BioRobotics).

Since the obtained PCR clones were expected to contain multiple overlapping clones of the NPY receptor cDNA, 80 clones out of the 5,760 clones were randomly selected, and their nucleotide sequences were partially determined. To determine the nucleotide sequence, plasmid DNA purified by the plasmid automatic isolating system PI100sigma (Kurabo) was used as a template. The sequence reactions were performed using the dye-primer-cycle sequencing kit FS (Perkin Elmer), and the reaction products were separated by electrophoresis using the DNA sequencer 377 (Perkin Elmer). The homology search of the obtained sequence using the BLAST program of the Wisconsin package (Genetic Computer Group) showed that 29 out of the 80 clones were the cDNAs encoding the coiled-coil like protein 1 (GenBank Accession Number U79024) while 17 clones were those of the neuropeptide Y receptor Y1 (Z11504). Then, these two cDNA fragments were used as a probe for hybridization with the filters containing a library of the degenerated PCR amplified fragments. Probes were prepared by amplifying the insert of the respective clones by PCR, purifying the products using the Wizard PCR purification kit (Promega), and labeling them with [α-$^{32}$P] dCTP using the Prime-It II random primer labeling kit (Stratagene). Colony hybridization was performed according to the standard method (Sambrook et al., Molecular Cloning: A laboratory manual 2$^{nd}$ edition (1989)). Colonies that were negative for either the coiled-coil like protein 1 or the neuropeptide Y receptor Y1 were selected and their partial nucleotide sequences were determined. For DNA sequencing, the insert fragment of each clone was amplified by PCR from the culture medium, purified using the PCR product purification kit (Amersham), and used as a template. The sequence reactions were performed using the dye-primer-cycle sequencing kit FS (Perkin Elmer), and the reaction products were separated by electrophoresis using the DNA sequencer 377 (Perkin Elmer). The obtained sequences were analyzed by the homology search using the BLAST program of the Wisconsin package (Genetic Computer Group), and, as a result, a clone which has significant homology to the muscarinic acetylcholine receptor M5 (GeneBank Accession Number M22926) was found. The clone has been deposited at the National Institute of Bioscience and Human-Technology, Agency of Industrial Science and Technology.

Name of the depositary institution:
National Institute of Bioscience and Human-Technology, Agency of Industrial Science and Technology, MITI.

Address of the depositary institution:
1-1-3 Higashi, Tsukuba, Ibaraki 305-8566, Japan.

Date of deposit: Dec. 25, 1997.

Accession Number: FERM BP-6575

Next, in order to isolate the full-length cDNA of the gene, cDNA libraries were prepared from rat thalamus and hypothalamus. cDNA was synthesized according to the protocol accompanying the cDNA synthesizing kit (Stratagene), and the vector pEF1× and the host XL1-blue MRF' (Stratagene) were used.

The pEF1× is a refined derivative of the pcDNA3 (Invitrogen) prepared as follows.

(1) Preparation of the Human EF1α Promoter (GenBank Accession Number J04617)

PCR was performed using human genomic DNA with primers (SEQ ID NO:6/CGAGGATCCGTGAGGCTCCG- GTCCCGTC; SEQ ID NO:7/CGGGTAAGCTTCACGA-CACCTGAAATGGAAGA). The products were digested with BamHI (TaKaRa) and HindIII (TaKaRa), and subcloned into the plasmid vector pUC19 (TaKaRa). The resulting plasmid was digested with XhoI, blunt-ended with Klenow fragment (TaKaRa), and self-ligated using the DNA ligation kit (TaKaRa). The resulting plasmid was digested with BamHI and HindIII, and the insert was recovered.

(2) Alteration of pcDNA3 pcDNA3 was digested with MluI (TaKaRa), blunt-ended with Klenow fragment (TaKaRa), and self-ligated using the DNA ligation kit. The resulting plasmid was digested with AflIII (New England Biolabs) and SmaI (TaKaRa), blunt-ended with Klenow fragment (TaKaRa), and self-ligated using the DNA ligation kit. Then, the obtained plasmid was digested with BglII (TaKaRa) and HindIII, and the fragment from which the CMV promoter was removed was recovered and ligated with the insert fragment recovered in (1) using the DNA ligation kit to construct pEF1×.

Next, the nucleotide sequence of the cDNA fragment was used to synthesize oligonucleotide probe (SEQ ID NO:8/CCTTCTGCATCCCATTGTACGTACC). According to the protocol of the gene trapper cDNA positive selection system (GIBCO BRL), multiple clones were obtained from the above-prepared cDNA libraries derived from rat thalamus and hypothalamus. Then, colony hybridization was performed using the cDNA insert of the above-isolated clone (FERM P-16572) as a probe, and a positive clone was obtained. This clone has been deposited with the National Institute of Bioscience and Human-Technology, Agency of Industrial Science and Technology.

Name of the depositary institution:
National Institute of Bioscience and Human-Technology, Agency of Industrial Science and Technology, MITI.

Address of the depositary institution:
1-1-3 Higashi, Tsukuba, Ibaraki 305-8566, Japan.

Date of deposit: Dec. 25, 1997.

Accession Number: FERM BP-6574

The insert fragment of the clone was 2.7 kb long. Plasmid DNA was prepared with the QIAprep Midi Kit (QIAGEN), and the complete nucleotide sequence was determined using the shotgun cloning method (Sambrook et al., Molecular Cloning: A laboratory manual $2^{nd}$ edition (1989)). cDNA fragmentation was performed using the closed sonifier biomaterial treating system Biorupter (Tousou Denki), and the DNA fragments were separated by electrophoresis on a 2% agarose gel. Fragments of around 0.6 kb were purified using the gene clean spin kit (bio101), blunt-ended with T4 DNA polymerase (TaKaRa), and cloned into HincII-BAP-treated pUC118 vector. XL1-Blue was used as a host cell, and transformed using the E. coli pulser (BioRad). The obtained shotgun clones were sequenced using the dye-primer cycle sequencing kit FS (Perkin Elmer), or the dye-terminator cycle sequencing kit FS (Perkin Elmer). The resulting sequences were combined and edited to get the complete nucleotide sequence using the DNA sequencing software Sequencher (Hitachi Software). The complete nucleotide sequence was composed of 2700 bp, and turned out to be encoding a protein of 413 amino acids (SEQ ID NO:5). Because there is a stop codon in the 5' region of the open reading frame, the cDNA is presumed to include the entire coding region (SEQ ID NO:2). When this sequence was translated into the amino acid sequence, the hydrophobicity plot identified seven transmembrane regions from 1 to 7 (FIG. 1).

In addition, the open reading frame size was approximately 1.2 kb, which is similar to that of the known G protein-coupled receptors. G protein-coupled receptor proteins have common features in their amino acid sequences, and thus form a protein family. As a result of the homology search using the amino acid sequence encoded by the isolated cDNA, the encoded protein was found to be a novel receptor protein having a homology of 26%, 25%, and 29% to known G protein-coupled receptors: bovine muscarinic acetylcholine receptor M3 protein (Lee et al., Biochim. Biophys. Acta, 1223:151-154 (1994)), human muscarinic acetylcholine receptor M5 protein (Bonner et al., Neuron, 1:403-410 (1988)), and mouse α2A adrenoreceptor (Link et al., Mol. Pharmacol., 42:16-27 (1992)), respectively.

Example 2

Isolation of the Human G Protein-Coupled Receptor Gene

The obtained rat sequence was subjected to EST search to reveal a fragment of the human homologue (gene bank NID: 946030 and NID: 901756). Human fetal brain cDNA was amplified by PCR using the specific primers IF01 (SEQ ID NO:9/CTTCCGCCGGGCCTTCACCAA) and IR02 (SEQ ID NO:10/ACAGACACGGCGGGGCTCAC) (probe 1). A human λ EMBL3 SP6/T7 genomic library (Clontech) of a size of $1.2 \times 10^6$ pfu was screened using probe 1 according to standard plaque hybridization procedures. Two positive clones were thus isolated. The obtained phage-clones were digested with SacI, and three bands of a clone were subcloned. These fragments, termed I1 (SEQ ID NO:11), I3 (SEQ ID NO:12) and I5 (SEQ ID NO:13), were sequenced and a hypothetical sequence was speculated by comparing with the rat homologue. I1 and I3 were subjected to PCR amplification using specific primers YS03 (SEQ ID NO:14/TGAACGCTTCGGGGGCGCTG) and YS05 (SEQ ID NO:15/GAGATGGCGAGGTTGAGCAGG), and YS12 (SEQ ID NO:16/GGCTCCAAGCCATCGGCGTC) and YS14 (SEQ ID NO:17/CTCACTTCCAGCAGTGCTCC), respectively, and the PCR products were termed probe 2 and probe 3, respectively. Human hypothalamus cDNA ($1.3 \times 10^6$ phage) was plated at a density of $5.6 \times 10^4$ pfu/150 mm plate. The obtained sub-pools were checked by PCR using the primers YS03 and YS05. One positive sub-pool was screened in the same method as the screening of the genomic library, using probe 2. One cDNA clone containing the region between 5'UTR and TM5 was obtained and named cDNA clone 1.

Probe 4 was amplified by PCR from cDNA clone 1 using the primers YS07 (SEQ ID NO:18/GCCTCCGCACCCA-GAACAAC) and YS10 (SEQ ID NO:19/TGCGCCTCTG-GATGTTCAG). Screening of the human hippocampus library ($3 \times 10^6$ pfu) was done in the same method as the genomic library, using probe 3 and probe 4. A few clones were obtained and the longest one, termed cDNA clone 2, was sequenced. It has the region between TM2 and 3'UTR. cDNA clone 1 was digested with SacII, and the 3.3 kb band, which contained vector and the 5'-end region, was treated by shrimp alkaline phosphatase. cDNA clone 2 was also digested with SacII, and the 1.7 kb fragment was ligated into the 3.3 kb fragment from cDNA clone 1. The clone into which this ligated fragment was inserted has been deposited with the National Institute of Bioscience and Human-Technology, Agency of Industrial Science and Technology.

Name of the depositary institution:
   National Institute of Bioscience and Human-Technology, Agency of Industrial Science and Technology, MITI.

Address of the depositary institution:
   1-1-3 Higashi, Tsukuba, Ibaraki 305-8566, Japan.

Date of deposit: Dec. 17, 1998.

Accession Number: FERM BP-6609

Human BG2 cDNA nucleotide sequence is shown in SEQ ID NO:21, and the amino acid sequence of the protein encoded by the cDNA in SEQ ID NO:20.

Human BG2 protein had 32%, 28%, and 27% homology to known G protein-coupled receptors: human α-2C-1 adrenoreceptor (Regan et al., Proc. Natl. Acad. Sci. USA, 85:6301-6305 (1988)), mouse β-1 adrenoreceptor (Jasper et al., Biochim. Biophys. Acta, 1178:307-309 (1993)), and human muscarinic acetylcholine receptor M3 protein (Peralta et al., EMBO J., 6:3923-3929 (1987)), respectively.

Example 3

Northern Blot Analysis

Probe 4 was labeled with $^{32}$P γ-dCTP (Amersham, Prime It II) and used as cDNA probe for the detection of human BG2. Human Multiple Tissue Northern (MTN) Blots Membrane was purchased from Clontech. After prehybridization of the membrane at 68° C. for 30 min in ExpressHyb solution (Clontech), it was hybridized with the probe at 68° C. for 1 hr (final concentration of the probe was $1.5 \times 10^6$ cpm/ml). The blot was rinsed with 2×SSC containing 0.1% SDS at 42° C. for 30 min, and the final wash was done at 50° C. for 30 min in 0.1×SSC containing 0.1% SDS. The blot was then exposed at −80° C. for 2.5 days to Kodak autoradiographic film.

For the detection of the rat BG2, probe was prepared by PCR-amplifying using the rat BG2 cDNA as a template with sense primer MF2 (SEQ ID NO:22/TGCATCCCATTG-TACGTNCC) and antisense primer MR1 (SEQ ID NO:24/TGCTCTGGGACACCATCTTC), purifying the amplified products by electrophoresis on an agarose gel, and labeling them as described above for human gene.

Figure 2:
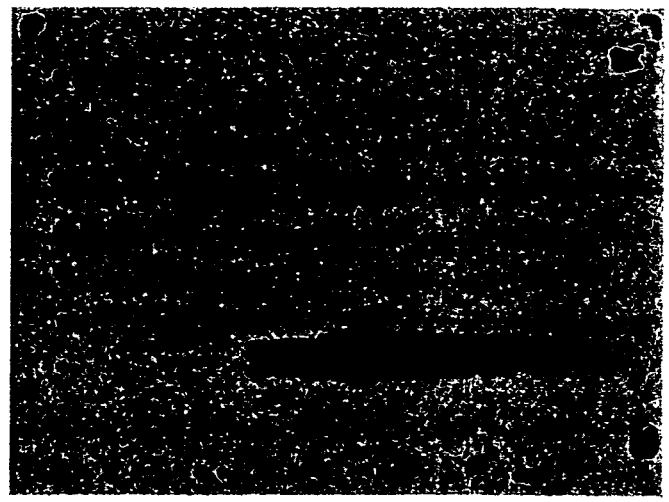
FIG. 2 shows the results of northern blot analysis of the tissue-specific expression of the human and rat BG2 genes.
Figure 2:
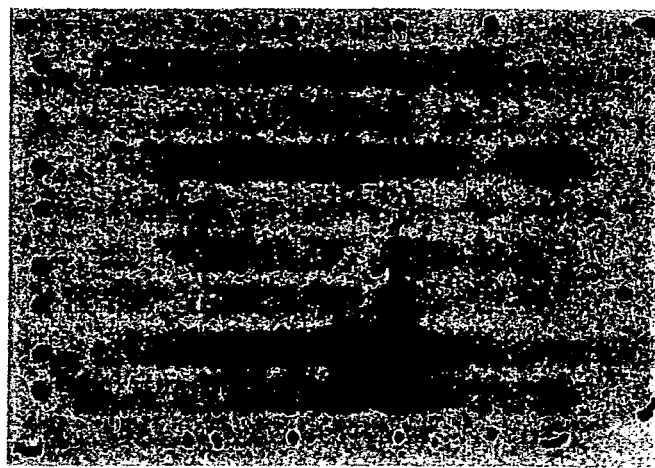

Blotting membrane used was Rat MTN (Multiple Tissue Northern) blot (Clontech). Hybridization was performed at 42° C. overnight in hybridization buffer (50% formamide, 4×SSPE, 1% SDS, 0.5% BLOTTO, and 100 µg/ml salmon sperm DNA). The membrane was washed at 65° C. in 0.1×SSC containing 0.1% SDS, and then exposed to the Kodak autoradiography film at −80° C. overnight. The results showed that the human and rat BG2 genes are strongly expressed particularly in the brain (FIG. 2).

Example 4

In Situ Hybridization

Adult male Sprague-Dawley rats (Charles River Japan) aged 13 to 18 weeks, were anesthetized with inhalation of ether, connected to a rotary pump and infused with chilled 4% paraformaldehyde in phosphate buffer (pH 7.2) via a cannula inserted into the left ventricle. After perfusion, brain, pituitary gland, and spinal cord were removed and dissected to sagittal or coronal sections. The tissue specimens were postfixed with the same fixative overnight at 4° C. The following process was carefully done to avoid RNase contamination. Tissue specimens were embedded in paraffin wax in a routine manner, then paraffin sections were cut into a thickness of 6 µm by rotary microtome (Model HM 355; MICROM Laborgerate GmbH). The sections were stored in moisture free condition at −20° C. until proceeded to in situ hybridization.

For preparation of rat BG2 sense and antisense RNA probes, the cDNA fragment amplified by PCR from MP-21 plasmid DNA using a sense primer MF2 (SEQ ID NO:22/TGCATCCCATTGTACGTNCC) and antisense primer MR3 (SEQ ID NO:23/ATCATTAGGAGCGTGTANGG) was cloned into pZErO-2 vector (Invitrogen). The RNA probes were labeled with digoxigenin using DIG RNA Labeling Kit (Boehringer Mannheim). The paraffin sections were de-paraffinized with xylene and transferred to distilled water after rinsing with a graded series of ethanol. In situ Hybridization Reagents (ISHR, Code No. 316-01951; Nippon Gene) were used as reagents without digoxigenin-labeled RNA. The sections were incubated with two changes of phosphate buffer saline (PBS;ISHR 1) for 1 min and 10 min. The sections were treated with proteinase K (ISHR 6) for 10 min at 37° C. Acetylation was done with acetylation buffer (ISHR 3) containing acetic anhydride (ISHR 4) for 15 min, followed by quenching with PBS/glycine buffer (ISHR 2) for 20 min at room temperature. After that, the sections were rinsed twice with 4×SSC (ISHR 5) for 10 min and then rinsed with PBS buffer for 10 min. After pre-hybridization with 50% formamide/2×SSC for 30 min at room temperature, hybridization was performed for 16 hr at 42° C. using digoxigenin-labeled RNA probe (1 µg/ml).

Post hybridization washing was performed twice with 50% formamide/2×SSC for 10 min at 42° C. Then, the sections were treated with RNase A (ISHR10)/NET buffer (ISHR 9) for 30 min at 37° C. after rinsing with NET buffer (ISHR 9) for 5 min at 37° C. After washing twice with 0.1×SSC buffer (ISHR 11) for 20 min, the sections were transferred and the digoxigenin used for labeling was detected using the Digoxigenin Detection Kit (Boehringer Manheim). Then, the sections were rinsed for 1 min at room temperature with buffer (Buffer 1) containing 100 mM Tris-Hcl and 150 mM NaCl and incubated with blocking reagent (Buffer 2) for 30 min at room temperature. The sections were incubated with anti-digoxigenin alkaline phosphatase-labeled antibody for 60 min at room temperature. After washing with Buffer 1 for 15 min and Buffer 3 for 2 min at room temperature, the sections were incubated with NBT/X-phosphate solution diluted with Buffer 3 for 12 to 14 hr at room temperature. The sections were mounted with glycerol or Permount after washing with Buffer 4.

Figure 3:
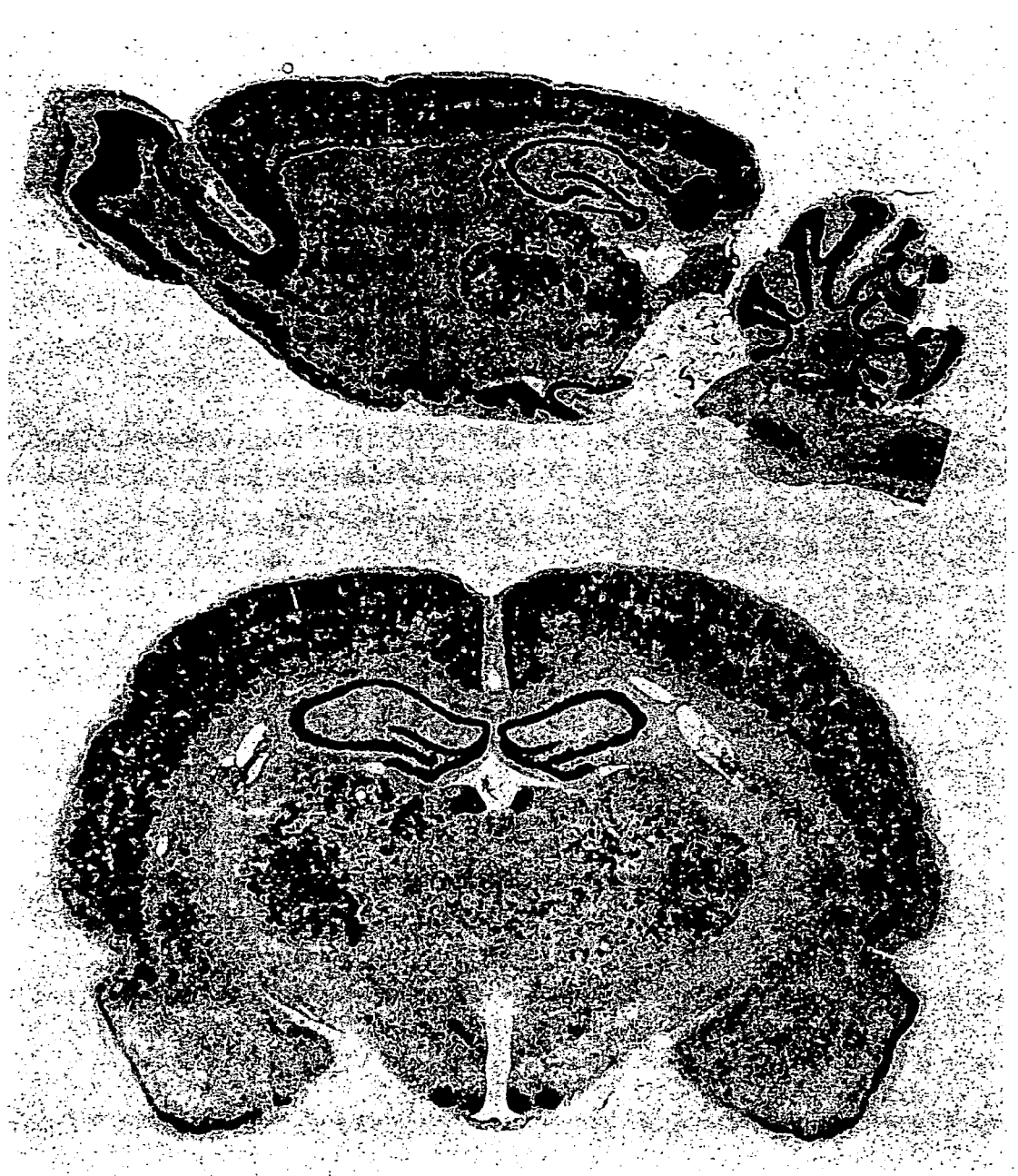
FIG. 3 shows the results of in situ hybridization analysis of the location of the rat BG2 gene expression in the brain.
Figure 4:
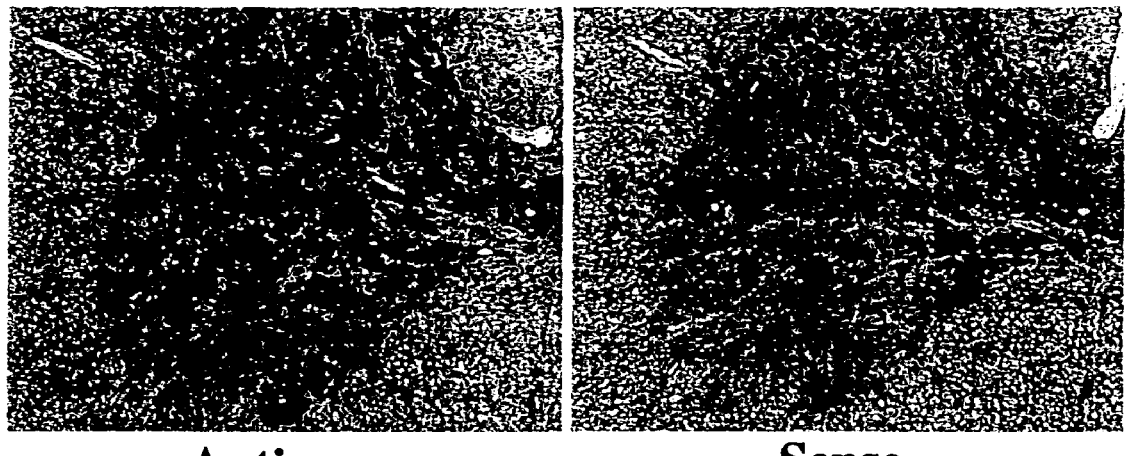
FIG. 4 shows the results of in situ hybridization analysis of the location of the rat BG2 gene expression in the spinal cord. "Sense" and "Antisense" indicate the results using sense RNA probe (not hybridizing with mRNA; negative control), and antisense RNA probe (hybridizing with mRNA), respectively.

As a result, as shown in FIGS. 3 and 4, BG2 cDNA probe was strongly hybridized to the hippocampus and the spinal cord. A medium degree of hybridization signal was also detected in hypothalamus, thalamus, and cerebellum.

Example 5

Preparation of Human BG2-Expressing Cells

Human BG2 expression vector was prepared using pIRESneo and pIREShyg (CLONTECH). To facilitate cloning of the human BG2 gene, a plasmid in which neomycin resistance gene of pIRESneo was replaced with a hygromycin resistance gene of pIREShyg was prepared, and the human BG2 gene was cloned thereto to prepare the expression vector.

This human BG2 expression vector was introduced by lipofection method into HEK 293cells in which β-lactamase gene was ligated downstream of CRE sequence (purchased from Aurora). For introducing the gene, Lipofectamine PLUS reagent (GIBCO-BRL) was used and the experimental manipulation was performed according to the attached manual.

Human BG2-expressing cells were selected by placing cells in a medium containing hygromycin, and cells which grew in the medium were used for a functional assay as human BG2-expressing cells. The expression of BG2 gene was confirmed by the RT-PCR method.

Example 6

Measurement of Intracellular cAMP Concentration

The intracellular cAMP concentration was measured by the method of Zlokarmik et al. (Science, 1998, 279:84). In the method of Zlokarmik et al., intracellular cAMP concentration was measured by introducing the gene in which β-lactamase gene was ligated downstream of the sequence that increased transcription activity of a gene downstream thereof dependently on the increase of intracellular cAMP concentration (CRE: cAMP responsible element), and by measuring fluorescence changes in florescent substrates to which an activity of β-lactamase transcribed and translated by the change of cAMP concentration in the cells was added.

Moreover, to measure the decrease of intracellular cAMP concentration mediated by the bound G protein in seven-transmembrane receptors, an activity of β-lactamase depending on the intracellular cAMP concentration was increased by adding forskolin and the decrease of cAMP in cells was measured with the decrease of β-lactamase activity when a ligand was reacted.

The cells in which the above reporter gene and human BG2 were expressed were washed with PBS(-) buffer (GIBCO-BRL) twice, Cell-dissociation buffer (GIBCO-BRL) was added thereto, and the cells were warmed at 37° C. in a $CO_2$ incubator for 3 min and dissociated from a flask by gently tapping the incubation flask. The cells were collected by centrifugation, suspended in Opti-MEM medium (GIBCO-BRL) containing 0.1% BSA (Sigma) to count the number of cells, and adjusted to $8 \times 10^4$ cells/ml.

To 1 μl of DMSO solution containing 100 μg/ml of each drug, 50 μl of Opti-MEM medium (GIBCO-BRL) containing 0.1% BSA (Sigma) to which forskolin (Sigma) was added at a final concentration of 0.5 μM was added in advance to prepare the reaction solution. To this reaction solution, 50 μl of the cells adjusted to the above cell number was added to initiate the reaction, and warmed at 37° C. in the $CO_2$ incubator for 3 hours.

Subsequently, using a kit purchased from Aurora, Solution A [1 mM CCF2-AM/dry DMSO solution], Solution B [100 mg/ml Pluronic 127, 0.1% acetic acid in DMSO], and Solution C [24% w/w PEG-400, 18% TR40, water] were mixed at a ratio of 12 μl: 120 μl: 2 ml to prepare a pigment introduction buffer. To the above reaction solution, 20 μl of the pigment introduction solution was added, and placed for 1 hour at room temperature to introduce into cells a fluorescent pigment (CCF2-AM) which is a substrate for β-lactamase, and change of intracellular cAMP concentration was measured by obtaining fluorescence at fluorescence wave length 460 nm (decomposed CCF) and 530 nm (CCF) with excitation wave length 409 nm and by calculating (EM460/EM530).

Figure 5:
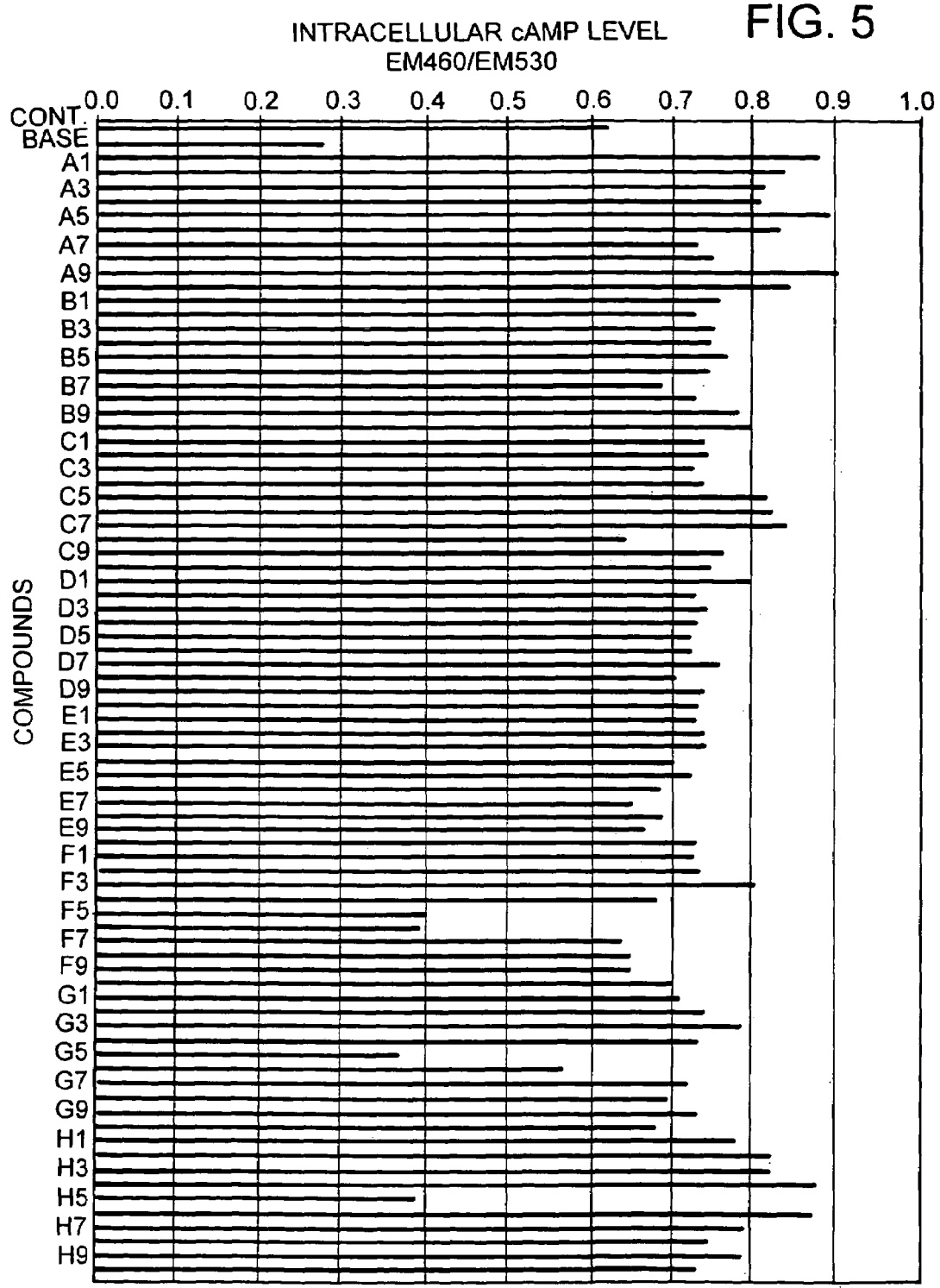
FIG. 5 shows the results of detecting a change of cAMP concentration after reacting various drugs on human BG2-expressing cells. Intracellular cAMP concentration was increased by forskolin, an activator of adenylate cyclase (Lane: control), and a change of intracellular cAMP concentration in case of reacting various test compounds was measured (Lanes: A1 to H10) using the method of Zlokarmik et al. (Science, 1998,279:84). A level of intracellular cAMP concentration in case of not reacting forskolin was shown in Lane: base.

Each drug was tested at the concentration of 1 μg/ml, and in BG2-expressing cells, the ratio of EM460/EM530 reduced to 35% of the control by histamine (when the value of the ratio in the control was 100, and the value of the ratio in the absence of forskolin was 0). The same phenomenon was observed in R(−)-α-methylhistamine, imetit, and N-α-methylhistamine, which are histamine analogue agonists (FIG. 5). Specifically, intracellular cAMP concentration was decreased in BG2-expressing cells by histamine. This intracellular cAMP concentration-reducing phenomenon by histamine was a phenomenon specific to BG2-expressing cells and was not observed in control cells expressing nothing.

Other test drugs (carbachol, which is an agonist for a muscarinic acetylcholine receptor; serotonine, which is an agonist for a serotonine receptor; and dopamine, which is an agonist for a dopamine receptor, etc.) at the concentration of 1 μg/ml did not reduce intracellular cAMP concentration. This shows that the BG2 receptor is a histamine receptor.

Table 1 below shows the compounds used in the experiment.

TABLE 1

| | 1 | 2 | 3 | 4 | 5 |
|---|---|---|---|---|---|
| A | Albutanol hemisulfate | DSP-4 hydrochloride | Phenoxy-benzamine hydrochloride | (±)-Chlorphenamine maleate | (−)-Epinephrine bitartrate |
| B | Alprenolol hydrochloride | Beneoxtamine tetrahydrochloride | Bretylum tosylate | (±)-CGP-12177A hydrochloride | None |
| C | (±)-Atenolol | MHPG sulfate potassium | BU224 hydrochloride | Clobenpropil dihydrochloride | None |
| D | Agrmaline sulfate | 6-Fluoro-norepinephrine hydrochloride | B-HT 933 dihydrochloride | Cirazoline hydrochloride | Guanabenzamide acetate |
| E | AGN 192403 hydrochloride | Xytamine hydrochloride | B-HT 920 dihydrochloride | CGP 20712A methanesulfonate | L-Histidine hydrochloride |
| F | Cloridine hydrochloride | Benoxathian hydrochloride | BRL 37344 sodium | Dimaprit dihydrochloride | Histamine dihydrochloride |
| G | p-Amino-cloridine hydrochloride | MHPG piperazine | CGS-12066A dimaleate | Diphenhydramine hydrochloride | Histamine, R(−)-alpha-methyl-, dihydrochloride |
| H | (±)-threo-DOPS | WB-4101 hydrochloride | Cimetidine | Dobutamine hydrochloride | Histamine, N-alpha-methyl-, dihydrochloride |

TABLE 1-continued

|   | 6 | 7 | 8 | 9 | 10 |
|---|---|---|---|---|---|
| A | Histamine, 1-methyl-, dihydrochloride | Methoxamine hydrochloride | Oxymetazoline hydrochloride | Phenylphrine hydrochloride | Thiopenamide maleate |
| B | Hydrochlorothiazide | (±)-Nometanaphrine hydrochloride | Prazoain hydrochloride | None | Tripolennamine hydrochloride |
| C | (±)-isoproterenol hydrochloride | L(–)-Nonpinephrine bitartrate | (±)-Pinclobind | Protriptyaline hydrochloride | S(–)-Timolol maleate |
| D | p-Iodochloridine hydrochloride | None | Prazobind | Promethazine hydrochloride | Urapldii hydrochloride |
| E | ICI 118,551 hydrochloride | Nisoxatine hydrochloride | Pineolol | Ranitidine hydrochloride | UK 14,304 |
| F | Imetit dihydrochloride | Nylldrin hydrochloride | (±)-Propraneolol hydrochloride | Rauwolacine hydrochloride | Xylazine hydrochloride |
| G | Metanephrine hydrochloride | Naftopidil dihydrochloride | Pyrllamine maleate | SKF 91488 dihydrochloride | Yohimbine hydrochloride |
| H | (–)-alpha-Methyl-norepinephrine | (±)-Octopamine hydrochloride | Phentotamine mesylate | Triprolidine hydrochloride | YS-035 hydrochloride |

Example 7

Histamine Binding Experiment

Using R(–)-α-methylhistamine, which is a histamine analogue agonist, the binding experiment was conducted. The cells in which the BG2 receptor was expressed were washed with PBS(-) buffer (GIBCO-BRL) twice, Cell-dissociation buffer (GIBCO BRL) was added thereto, and the cells were warmed at 37° C. for 3 min in a $CO_2$ incubator and were dissociated from the incubation flask by gently tapping the flask. The cells were collected by centrifugation, and suspended in an assay buffer (Hanks' Balanced Salt Solution [GIBCO-BRL], 10 mM Hepes [Nacalai], 0.1% BSA [Sigma], pH 7.4 [adjusted with NAOH], the number of cells were counted, and the cells were adjusted to a final concentration of $0.6 \times 10^6$ cells/ml. The cells were warmed at 37° C. in the above assay buffer with 0.2 nM R(–)-α-methyl [imidazole-2,5(n)-3H]histamine (Amersham) for 30 min, and collected with Unifilter plate GF/B (Packard) treated with 0.5% polyethyleneimine (Wako). The nonspecific binding of the histamine analogues to cells was measured in the presence of 2 μM R(–)-α-methylhistamine (RBI). As a result, in BG2-expressing cells, whole binding:nonspecific binding is 4.4:1, and that in the control cells which did not express BG2 is 1.2:1. Thus, there is little difference between the amount of nonspecific binding in expressing cells and that in non-expressing cells. This indicates that the BG2 receptor specifically binds to the histamine analogues.

Example 8

Isolation of Rat BG2 Alternative Splicing Variants

Using the gene trapper cDNA positive selection system of Example 1 (2) (GIBCO BRL), numerous positive clones were obtained from rat thalamus- and hypothalamus-derived cDNA libraries. The analysis of these clones by the agarose gel electrophoresis with restriction enzyme decomposition and the determination of nucleotide sequences revealed that these clones contained clones different from rat BG2 (SEQ ID NO:5). Sequencing of these clones showed that these clones encode a protein composed of 445 amino acid residues, in which 32 amino acid residues were inserted into the third intracellular domain in comparison with rat BG2 (this clone was named "rat BG2-2"). The structure of BG2-2 is similar to that of human BG2 and shorter than human BG2 by 8 amino acid residues at the C-terminal side. These are considered to be rat BG2 alternative splicing variants transcribed from the identical gene.

Example 9

Preparation of Rat BG2-2-Expressing Cells (BG2-2-Stable Cell Line)

HEK293-CRE-BLA cells (Aurora) were cultured using the D-MEM/F-12 (1:1) mixed medium (GIBCO BRL) containing 10% fetal calf serum and 500 μg/ml G418 at 37° C. in the presence of 5% $CO_2$. Effectene Transfection Reagent (QIAGEN) was used for gene introduction.

A day prior to the gene introduction, cells were spread on a 6-well plate (NUNC) at $3 \times 10^5$ cells/well and 0.4 μg each of the rat BG-2 and BG2-2 expression vectors was introduced into them using 10 μl/well Effectene Transfection Reagent according to the attached manual. The cells were cultured at 37° C. in the presence of 5% $CO_2$ for 48 hours.

To isolate single cells into which the target gene was introduced, the cells were detached from a Petri dish by trypsin, and spread to a 96-well plate (NUNC) at 2000 to 250 cells/well. The cells were further cultured in selection medium containing hygromycin at 37° C. in the presence of 5% $CO_2$ for 14 days. Wells containing cells consisting of a single colony were only selected and cells were passage-cultured to prepare a stable cell line. From BG2-2-expressing cells prepared in this manner, total RNA was prepared and the amount of expression of the introduced BG2-2 was examined by Northern hybridization and cells with high expression were used for the following experiment. As a control, rat BG2-expressing cells were prepared in the same manner.

Example 10

Measurement of Intracellular cAMP Concentration (ELISA Method)

To measure the decrease of intracellular cAMP concentration mediated by the bound G protein in seven-transmembrane receptors, forskolin was added and intracellular cAMP concentration was measured when a ligand was reacted.

A day prior to the measurement of cAMP in cells, $2.5 \times 10^4$ cells/well were spread on a 24-well plate coated by poly-L-lysine (SUMIRON) and further incubated at 37° C. for 24 hours. The stable cell line was incubated at 37° C. for 15 min in D-MEM/F-12 (1:1) mixed medium free from serum, and further incubated at 37° C. for 15 min in D-MEM/F-12 (1:1) mixed medium containing 5 mM 3-isobutyl-1-methylxanthine (IBMX). In the presence of 10 μM forskolin, various concentrations of histamine were added thereto and cAMP in the cells was measured after the incubation at 37° C. for 15 min.

Intracellular cAMP was measured using the cyclic AMP enzymeimmunoassay (EIA) system (Amersham Pharmacia Biotech) according to the attached manual. At this time, cells were lysed with 200 µl of Lysis buffer per well and 20 µl of this cell extraction solution was used for cAMP measurement.

Figure 6:
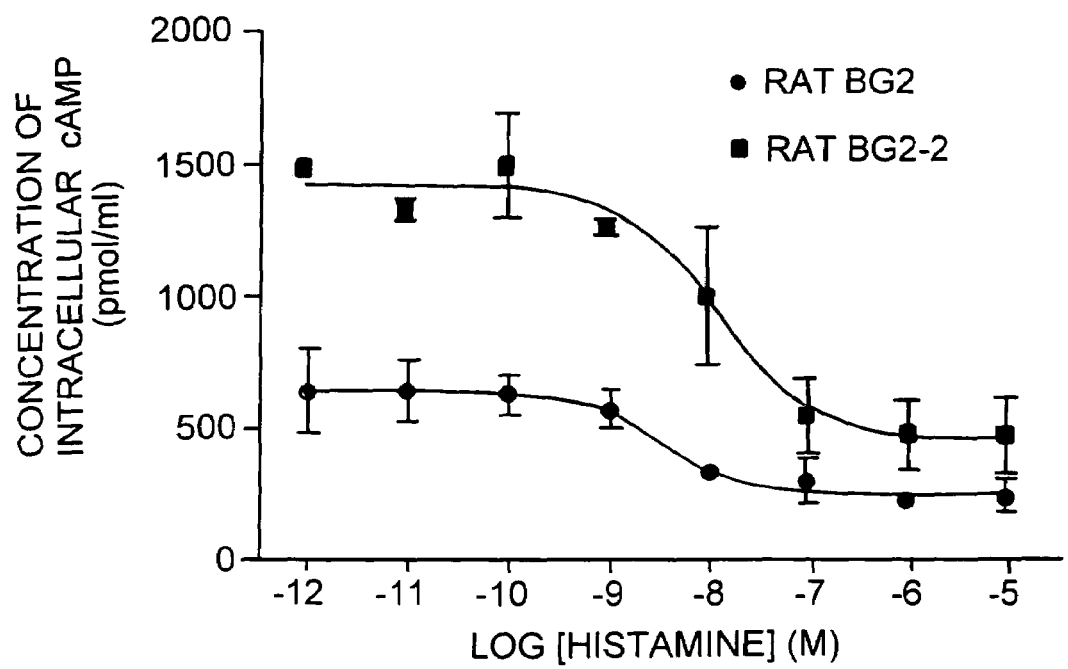
FIG. 6 shows the results of detecting a change of cAMP concentration after reacting histamine on the cells in which rat BG2-2 or BG2 was expressed in the presence of forskolin.

As a result, in rat BG2-2-expressing cells and rat BG2-expressing cells, the decrease of intracellular cAMP concentration, dependent on histamine concentration, was confirmed in the presence of 10 µM forskolin (FIG. 6). This indicates that both alternative splicing variants, rat BG2-2 and rat BG2 receptors, were coupled with Gai and that, specifically to histamine, they reduced intracellular cAMP concentration.

Example 11

Preparation of Cells Expressing Each BG2 (Human BG2, Rat BG2-2, or Rat BG2)

Vectors expressing each BG2 receptor were prepared using pEF1x (Biochemical and Biophysical Research Communications, 1998, 250:68-71). Each BG2 expression vector was introduced into COS7 cells by lipofection method. Genes were introduced using Lipofectamine PLUS reagent (GIBCO-BRL) according to the attached manual.

The cells were cultured at 37° C. for 24 hours in Dulbecco MEM medium (Asahi Techno Glass) to which fetal calf serum (Sigma) was added at a final concentration of 10%, in an incubator in which $CO_2$ concentration was adjusted to 5%. Then, the cells were used for preparing a membrane fraction for the histamine binding experiment.

Example 12

Histamine Binding Experiment For Each BG2 Receptor

The cells into which each BG2 receptor-expressing vector was introduced were crushed in 50 mM Tris-HCl pH 7.4 solution according to the standard method, uncrushed cells were removed by centrifuging at 1,000 g for 10 min, and supernatant was centrifuged at 100,000 g for 10 min to obtain a membrane fraction. The membrane fraction was resuspended in the 50 mM Tris-HCl pH 7.4 solution and centrifuged twice at 100,000 g for 10 min to finally obtain the membrane fraction. The membrane fraction obtained in this manner was suspended in 50 mM Tris-HCl pH 7.4 solution and used for the binding experiment.

By using N-α-methylhistamine, a histamine analogue agonist, the binding experiment was conducted and the binding constants were determined (Table 2). The above membrane fraction was warmed at 30° C. for 40 min with N-α-methylhistamine (NEN) in 50 mM Tris-HCl pH 7.4 solution and the cells were collected with Unifilter plate GF/C (Packard) treated in advance with 0.5% polyethyleneimine (Wako). The nonspecific biding of the histamine analogue to cells was measured in the presence of 2 µM N-α-methylhistamine (RBI). As a result, it was demonstrated that all cells expressing each BG2 receptor specifically bound to N-α-methylhistamine.

TABLE 2

| Receptor | Binding Constant(nM) |
| --- | --- |
| Human BG2 | 0.548 ± 0.0751 |
| Rat BG2 | 0.503 ± 0.0198 |
| Rat BG2-2 | 0.582 ± 0.0261 |

INDUSTRIAL APPLICABILITY

The present invention has provided a human-derived novel G protein-coupled receptor protein expressed in the brain, rat-derived protein corresponding to it, and their genes. Use of the receptors makes it possible to screen their ligands and compounds that are candidates for medicines. These ligands and candidate compounds would be useful in the diagnosis and treatment of diseases arising from disorders of signal transduction pathway mediated by the G protein-coupled receptor of the invention.

---

What is claimed is:

1. A method for identifying a compound that modulates a histamine binding activity, the method comprising:
   a) contacting (i) a polypeptide or (ii) a cell transfected with a nucleic acid encoding the polypeptide with a test compound, wherein the polypeptide comprises an amino acid sequence at least 95% identical to SEQ ID NO:20 or 25 and has a histamine binding activity; and
   b) determining whether the test compound modulates the histamine binding activity of the polypeptide or cell, thereby identifying a compound that modulates a histamine binding activity.

2. The method of claim 1, wherein the method further comprises determining whether the test compound modulates cellular cAMP concentration, cellular calcium concentration, a G protein activation, phospholipase C activation, or intracellular pH.

3. The method of claim 1, wherein the polypeptide comprises an amino acid sequence of a naturally occurring protein which binds to histamine.

4. The method of claim 1, wherein the polypeptide comprises the amino acid sequence of SEQ ID NO:20.

5. The method of claim 1, wherein the polypeptide comprises the amino acid sequence of SEQ ID NO:25.

6. The method of claim 1, wherein step a) comprises contacting the polypeptide with the test compound.

7. The method of claim 6, wherein the polypeptide comprises an amino acid sequence of a naturally occurring protein which binds to histamine.

8. The method of claim 6, wherein the polypeptide comprises the amino acid sequence of SEQ ID NO:20.

9. The method of claim 6, wherein the polypeptide comprises the amino acid sequence of SEQ ID NO:25.

10. The method of claim 1, wherein step a) comprises contacting the cell of (ii) with the test compound.

11. The method of claim 10, wherein the polypeptide comprises an amino acid sequence of a naturally occurring protein which binds to histamine.

12. The method of claim 10, wherein the polypeptide comprises the amino acid sequence of SEQ ID NO:20.

13. The method of claim 10, wherein the polypeptide comprises the amino acid sequence of SEQ ID NO:25.

14. A method for identifying a compound that modulates a histamine binding activity, the method comprising:
   a) contacting (i) a polypeptide or (ii) a cell transfected with a nucleic acid encoding the polypeptide with a test compound, wherein the polypeptide has a histamine binding activity and is encoded by a polynucleotide which hybridizes to a polynucleotide consisting of a complementary sequence of SEQ ID NO:21 or 26 under the conditions of 6×SSC, 40% formamide at 37° C., followed by a wash in 0.1×SSC containing 0.1% SDS at 62° C.; and
   b) determining whether the test compound modulates the histamine binding activity of the polypeptide or cell, thereby identifying a compound that modulates a histamine binding activity.

15. The method of claim 14, wherein the method further comprises determining whether the test compound modulates cellular cAMP concentration, cellular calcium concentration, a G protein activation, phospholipase C activation, or intracellular pH.

16. The method of claim 14, wherein the polypeptide comprises an amino acid sequence of a naturally occurring protein which binds to histamine.

* * * * *

UNITED STATES PATENT AND TRADEMARK OFFICE
CERTIFICATE OF CORRECTION

PATENT NO.         : 7,374,895 B2
APPLICATION NO.    : 11/447407
DATED              : May 20, 2008
INVENTOR(S)        : Hiraku Itadani et al.

Page 1 of 3

It is certified that error appears in the above-identified patent and that said Letters Patent is hereby corrected as shown below:

Title Page, (54) Title:

delete "GUANOSINE TRIPHOSPHATE (GTP) BINDING PROTEIN-COUPLED RECEPTOR PROTEINS THAT BIND HISTAMINE AND ARE EXPRESSED IN THE BRAIN"

insert -- ASSAY EMPLOYING A G PROTEIN-COUPLED HISTAMINE RECEPTOR EXPRESSED IN THE BRAIN --

Column 15, line 13:
    delete "AflII" and insert -- Afl III --

Column 20, Table 1:
    delete

"
TABLE 1

|   | 1 | 2 | 3 | 4 | 5 |
|---|---|---|---|---|---|
| A | Albutanol hemisulfate | DSP-4 hydrochloride | Phenoxybenzamine hydrochloride | (±)-Chlorpheniamine maleate | (−)-Epinephrine bitartrate |
| B | Alprenolol hydrochloride | Benzoxamine tetrahydrochloride | Bretylium tosylate | (±)-CGP-12177A hydrochloride | None |
| C | (±)-Atenolol | MHPG sulfate potassium | BU224 hydrochloride | Clobenpropil dihydrochloride | None |
| D | Agmatine sulfate | 6-Fluoro-norepinephrine hydrochloride | B-HT 933 dihydrochloride | Cirazoline hydrochloride | Guanabenzamide acetate |
| E | AGN 192403 hydrochloride | Xytamine hydrochloride | B-HT 920 dihydrochloride | CGP 20712A methanesulfonate | L-Histidine hydrochloride |
| F | Cloridine hydrochloride | Benoxathian hydrochloride | BRL 37344 sodium | Dimaprit dihydrochloride | Histamine dihydrochloride |
| G | p-Amino-cloridine hydrochloride | MHPG piperazine | CGS-12066A dimaleate | Diphenhydramine hydrochloride | Histamine, R(+)-alpha-methyl-, dihydrochloride |
| H | (±)-threo-DOPS | WB-4101 hydrochloride | Cimetidine | Dobutamine hydrochloride | Histamine, N-alpha-methyl-, dihydrochloride |

"

UNITED STATES PATENT AND TRADEMARK OFFICE
CERTIFICATE OF CORRECTION

PATENT NO. : 7,374,895 B2
APPLICATION NO. : 11/447407
DATED : May 20, 2008
INVENTOR(S) : Hiraku Itadani et al.

Page 2 of 3

It is certified that error appears in the above-identified patent and that said Letters Patent is hereby corrected as shown below:

Column 20, Table 1:
and replace with

TABLE 1

|   | 1 | 2 | 3 | 4 | 5 |
|---|---|---|---|---|---|
| A | Albuterol hemisulfate | DSP-4 hydrochloride | Phenoxybenzamine hydrocholoride | (±)-Chlorpheniramine maleate | (−)-Epinephrine bitartrate |
| B | Alprenolol hydrochloride | Benextramine tetrahydrochloride | Bretylium tosylate | (±)-CGP-12177A hydrocholoride | None |
| C | (±)-Atenolol | MHPG sulfate potassium | BU224 hydrochloride | Clobenpropit dihydrochloride | None |
| D | Agmatine sulfate | 6-Fluoro-norepinephrine hydrochloride | B-HT 933 dihydrochloride | Cirazoline hydrochloride | Guanabenz acetate |
| E | AGN 192403 hydrochloride | Xylamine hydrochloride | B-HT 920 dihydrochloride | CGP 20712A methanesulfonate | L-Histidine hydrochloride |
| F | Clonidine hydrochloride | Benoxathian hydrochloride | BRL 37344 sodium | Dimaprit dihydrochloride | Histamine dihydrochloride |
| G | p-Amino clonidine hydrochloride | MHPG piperazine | CGS-12066A dimaleate | Diphenhydramine hydrochloride | Histamine, R(−)-alpha-methyl-, dihydrochloride |
| H | (±)-threo-DOPS | WB-4101 hydrochloride | Cimetidine | Dobutamine hydrochloride | Histamine, N(−)-alpha-methyl-, dihydrochloride |

Column 21, Table 1-continued:
delete

TABLE 1-continued

|   | 6 | 7 | 8 | 9 | 10 |
|---|---|---|---|---|---|
| A | Histamine, 1-methyl-, dihydrochloride | Methoxamine hydrochloride | Oxymetazoline hydrochloride | Phenylphrine hydrochloride | Thiopenamide maleate |
| B | Hydrochlorothiazide | (±)-Normetanaphrine hydrochloride | Prazosin hydrochloride | None | Tripolennamine hydrochloride |
| C | (±)-isoproterenol hydrochloride | L-(−)-Norepinephrine bitartrate | (±)-Pinclobind | Protriptyaline hydrochloride | S(−)-Timolol maleate |
| D | p-Iodochloridine hydrochloride | None | Prazobind | Promethazine hydrochloride | Urapidil hydrochloride |
| E | ICI 118,551 hydrochloride | Nisoxatine hydrochloride | Pineolol | Ranitidine hydrochloride | UK 14,304 |
| F | Imetit dihydrochloride | Nylidrin hydrochloride | (±)-Propranolol hydrochloride | Rauwolacine hydrochloride | Xylazine hydrochloride |
| G | Metanephrine hydrochloride | Nafropidil dihydrochloride | Pyrilamine maleate | SKF 91488 dihydrochloride | Yohimbine hydrochloride |
| H | (−)-alpha-Methyl-norepinephrine | (±)-Octopamine hydrochloride | Phentolamine mesylate | Triprolidine hydrochloride | YS-035 hydrochloride |

UNITED STATES PATENT AND TRADEMARK OFFICE
CERTIFICATE OF CORRECTION

PATENT NO. : 7,374,895 B2
APPLICATION NO. : 11/447407
DATED : May 20, 2008
INVENTOR(S) : Hiraku Itadani et al.

It is certified that error appears in the above-identified patent and that said Letters Patent is hereby corrected as shown below:

Column 21, Table 1-continued:
and replace with

TABLE 1-continued

|   | 6 | 7 | 8 | 9 | 10 |
|---|---|---|---|---|---|
| A | Histamine, 1-methyl-, dihydrochloride | Methoxamine hydrochloride | Oxymetazoline hydrochloride | Phenylephrine hydrochloride | Thioperamide maleate |
| B | Hydrochlorothiazide | (±)-Nometanaphrine hydrochloride | Prazosin hydrochloride | None | Tripelennamine hydrochloride |
| C | (±)-isoproterenol hydrochloride | L(-)-Norepinephrine bitartrate | (±)-Pindobind | Protriptyline hydrochloride | S(-)-Timolol maleate |
| D | p-Iodochlonidine hydrochloride | None | Prazobind | Promethazine hydrochloride | Urapldil hydrochloride |
| E | ICI 118,551 hydrochloride | Nisoxetine hydrochloride | Pindolol | Ranitidine hydrochloride | UK 14,304 |
| F | Imetit dihydrobromide | Nylidrin hydrochloride | (±)-Propranolol hydrochloride | Rauwolscine hydrochloride | Xylazine hydrochloride |
| G | Metanephrine hydrochloride | Naftopidil dihydrochloride | Pyrilamine maleate | SKF 91488 dihydrochloride | Yohimbine hydrochloride |
| H | (-)-alpha-Methyl-norepinephrine | (±)-Octopamine hydrochloride | Phentolamine mesylate | Triprolidine hydrochloride | YS-035 hydrochloride |

Signed and Sealed this

Seventeenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,374,895 B2                                    Page 1 of 3
APPLICATION NO.   : 11/447407
DATED             : May 20, 2008
INVENTOR(S)       : Hiraku Itadani et al.

It is certified that error appears in the above-identified patent and that said Letters Patent is hereby corrected as shown below:

Title Page, (54) and Column 1, lines 1-4, Title:

delete "GUANOSINE TRIPHOSPHATE (GTP) BINDING PROTEIN-COUPLED RECEPTOR PROTEINS THAT BIND HISTAMINE AND ARE EXPRESSED IN THE BRAIN"

insert -- ASSAY EMPLOYING A G PROTEIN-COUPLED HISTAMINE RECEPTOR EXPRESSED IN THE BRAIN --

Column 15, line 13:
    delete "AflII" and insert -- Afl III --

Column 20, Table 1:
    delete

"
TABLE 1

|   | 1 | 2 | 3 | 4 | 5 |
|---|---|---|---|---|---|
| A | Albutanol hemisulfate | DSP-4 hydrochloride | Phenoxy-benzamine hydrochloride | (±)-Chlorphenamine maleate | (-)-Epinephrine bitartrate |
| B | Alprenolol hydrochloride | Beneoxtamine tetrahydrochloride | Bretylium tosylate | (±)-CGP-12177A hydrochloride | None |
| C | (±)-Atenolol | MHPG sulfate potassium | BU224 hydrochloride | Clobenpropil dihydrochloride | None |
| D | Agmatine sulfate | 6-Fluoro-norepinephrine hydrochloride | B-HT 933 dihydrochloride | Cirazoline hydrochloride | Guanabenzamide acetate |
| E | AGN 192403 hydrochloride | Xytamine hydrochloride | B-HT 920 dihydrochloride | CGP 20712A methanesulfonate | L-Histidine hydrochloride |
| F | Cloridine hydrochloride | Benoxathian hydrochloride | BRL 37344 sodium | Dimaprit dihydrochloride | Histamine dihydrochloride |
| G | p-Amino-cloridine hydrochloride | MHPG piperazine | CGS-12066A dimaleate | Diphenhydramine hydrochloride | Histamine, R(-)-alpha-methyl-, dihydrochloride |
| H | (±)-threo-DOPS | WB-4101 hydrochloride | Cimetidine | Dobutamine hydrochloride | Histamine, N-alpha-methyl-, dihydrochloride |

"

UNITED STATES PATENT AND TRADEMARK OFFICE
CERTIFICATE OF CORRECTION

PATENT NO. : 7,374,895 B2  
APPLICATION NO. : 11/447407  
DATED : May 20, 2008  
INVENTOR(S) : Hiraku Itadani et al.

Page 2 of 3

It is certified that error appears in the above-identified patent and that said Letters Patent is hereby corrected as shown below:

Column 20, Table 1:
   and replace with

TABLE 1

|   | 1 | 2 | 3 | 4 | 5 |
|---|---|---|---|---|---|
| A | Albuterol hemisulfate | DSP-4 hydrochloride | Phenoxybenzamine hydrocholoride | (±)-Chlorpheniramine maleate | (−)-Epinephrine bitartrate |
| B | Alprenolol hydrochloride | Benextramine tetrahydrochloride | Bretylium tosylate | (±)-CGP-12177A hydrocholoride | None |
| C | (±)-Atenolol | MHPG sulfate potassium | BU224 hydrochloride | Clobenpropit dihydrochloride | None |
| D | Agmatine sulfate | 6-Fluoro-norepinephrine hydrochloride | B-HT 933 dihydrochloride | Cirazoline hydrochloride | Guanabenz acetate |
| E | AGN 192403 hydrochloride | Xylamine hydrochloride | B-HT 920 dihydrochloride | CGP 20712A methanesulfonate | L-Histidine hydrochloride |
| F | Clonidine hydrochloride | Benoxathian hydrochloride | BRL 37344 sodium | Dimaprit dihydrochloride | Histamine dihydrochloride |
| G | p-Amino clonidine hydrochloride | MHPG piperazine | CGS-12066A dimaleate | Diphenhydramine hydrochloride | Histamine, R(−)-alpha-methyl-, dihydrochloride |
| H | (±)-threo-DOPS | WB-4101 hydrochloride | Cimetidine | Dobutamine hydrochloride | Histamine, N(−)-alpha-methyl-, dihydrochloride |

Column 21, Table 1-continued:
   delete

TABLE 1-continued

|   | 6 | 7 | 8 | 9 | 10 |
|---|---|---|---|---|---|
| A | Histamine, 1-methyl-, dihydrochloride | Methoxamine hydrochloride | Oxymetazoline hydrochloride | Phenylphrine hydrochloride | Thiopenamide maleate |
| B | Hydrochlorothiazide | (±)-Normetanephrine hydrochloride | Prazosin hydrochloride | None | Tripolennamine hydrochloride |
| C | (±)-isoproterenol hydrochloride | L-(−)-Norepinephrine bitartrate | (±)-Pindolol | Protriptyaline hydrochloride | S(−)-Timolol maleate |
| D | p-Iodochloridine hydrochloride | None | Prazobind | Promethazine hydrochloride | Urapidil hydrochloride |
| E | ICI 118,551 hydrochloride | Nisoxatine hydrochloride | Pindolol | Ranitidine hydrochloride | UK 14,304 |
| F | Imetit dihydrochloride | Nylidrin hydrochloride | (±)-Propranolol hydrochloride | Rauwolacine hydrochloride | Xylazine hydrochloride |
| G | Metanephrine hydrochloride | Nafiopidil dihydrochloride | Pyrilamine maleate | SKF 91488 dihydrochloride | Yohimbine hydrochloride |
| H | (−)-alpha-Methyl-norepinephrine | (±)-Octopamine hydrochloride | Phentolamine mesylate | Triprolidine hydrochloride | YS-035 hydrochloride |

"                                                                                                                    "

UNITED STATES PATENT AND TRADEMARK OFFICE
CERTIFICATE OF CORRECTION

PATENT NO.       : 7,374,895 B2
APPLICATION NO.  : 11/447407
DATED            : May 20, 2008
INVENTOR(S)      : Hiraku Itadani et al.

It is certified that error appears in the above-identified patent and that said Letters Patent is hereby corrected as shown below:

Column 21, Table 1-continued:
    and replace with

TABLE 1-continued

|   | 6 | 7 | 8 | 9 | 10 |
|---|---|---|---|---|---|
| A | Histamine, 1-methyl-, dihydrochloride | Methoxamine hydrochloride | Oxymetazoline hydrochloride | Phenylephrine hydrochloride | Thioperamide maleate |
| B | Hydrochlorothiazide | (±)-Nometanaphrine hydrochloride | Prazosin hydrochloride | None | Tripelennamine hydrochloride |
| C | (±)-isoproterenol hydrochloride | L(-)-Norepinephrine bitartrate | (±)-Pindobind | Protriptyline hydrochloride | S(-)-Timolol maleate |
| D | p-Iodochlonidine hydrochloride | None | Prazobind | Promethazine hydrochloride | Urapldil hydrochloride |
| E | ICI 118,551 hydrochloride | Nisoxetine hydrochloride | Pindolol | Ranitidine hydrochloride | UK 14,304 |
| F | Imetit dihydrobromide | Nylidrin hydrochloride | (±)-Propranolol hydrochloride | Rauwolscine hydrochloride | Xylazine hydrochloride |
| G | Metanephrine hydrochloride | Naftopidil dihydrochloride | Pyrilamine maleate | SKF 91488 dihydrochloride | Yohimbine hydrochloride |
| H | (-)-alpha-Methyl-norepinephrine | (±)-Octopamine hydrochloride | Phentolamine mesylate | Triprolidine hydrochloride | YS-035 hydrochloride |

This certificate supersedes the Certificate of Correction issued February 17, 2009.

Signed and Sealed this

Seventeenth Day of March, 2009

JOHN DOLL
*Acting Director of the United States Patent and Trademark Office*

SEQUENCE LISTING

<160> NUMBER OF SEQ ID NOS: 26

<210> SEQ ID NO 1
<211> LENGTH: 413
<212> TYPE: PRT
<213> ORGANISM: Rattus norvegicus

<400> SEQUENCE: 1

```
Met Glu Arg Ala Pro Pro Asp Gly Leu Met Asn Ala Ser Gly Thr Leu
 1               5                  10                  15

Ala Gly Glu Ala Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
        35                  40                  45

Val Leu Gly Asn Ala Leu Val Met Leu Ala Phe Val Ala Asp Ser Ser
    50                  55                  60

Leu Arg Thr Gln Asn Asn Phe Phe Leu Leu Asn Leu Ala Ile Ser Asp
65                  70                  75                  80
```

```
Phe Leu Val Gly Ala Phe Cys Ile Pro Leu Tyr Val Pro Tyr Val Leu
                 85                  90                  95

Thr Gly Arg Trp Thr Phe Gly Arg Gly Leu Cys Lys Leu Trp Leu Val
            100                 105                 110

Val Asp Tyr Leu Leu Cys Ala Ser Val Phe Asn Ile Val Leu Ile
        115                 120                 125

Ser Tyr Asp Arg Phe Leu Ser Val Thr Arg Ala Val Ser Tyr Arg Ala
    130                 135                 140

Gln Gln Gly Asp Thr Arg Arg Ala Val Arg Lys Met Ala Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
                180                 185                 190

Phe Tyr Asn Trp Tyr Phe Leu Ile Thr Ala Ser Thr Leu Glu Phe Phe
            195                 200                 205

Thr Pro Phe Leu Ser Val Thr Phe Phe Asn Leu Ser Ile Tyr Leu Asn
    210                 215                 220

Ile Gln Arg Arg Thr Arg Leu Arg Leu Asp Gly Gly Arg Glu Ala Gly
225                 230                 235                 240

Pro Glu Pro Pro Pro Asp Ala Gln Pro Ser Pro Pro Ala Pro Pro
                245                 250                 255

Ser Cys Trp Gly Cys Trp Pro Lys Gly His Gly Glu Ala Met Pro Leu
                260                 265                 270

His Ser Ser Gly Ser Ser Ser Arg Gly Thr Glu Arg Pro Arg Ser Leu
            275                 280                 285

Lys Arg Gly Ser Lys Pro Ser Ala Ser Ser Ala Ser Leu Glu Lys Arg
    290                 295                 300

Met Lys Met Val Ser Gln Ser Ile Thr Gln Arg Phe Arg Leu Ser Arg
305                 310                 315                 320

Asp Lys Lys Val Ala Lys Ser Leu Ala Ile Ile Val Ser Ile Phe Gly
                325                 330                 335

Leu Cys Trp Ala Pro Tyr Thr Leu Leu Met Ile Ile Arg Ala Ala Cys
                340                 345                 350

His Gly Arg Cys Ile Pro Asp Tyr Trp Tyr Glu Thr Ser Phe Trp Leu
            355                 360                 365

Leu Trp Ala Asn Ser Ala Val Asn Pro Val Leu Tyr Pro Leu Cys His
    370                 375                 380

Tyr Ser Phe Arg Arg Ala Phe Thr Lys Leu Leu Cys Pro Gln Lys Leu
385                 390                 395                 400

Lys Val Gln Pro His Gly Ser Leu Glu Gln Cys Trp Lys
                405                 410
```

<210> SEQ ID NO 2
<211> LENGTH: 1239
<212> TYPE: DNA
<213> ORGANISM: Rattus norvegicus
<220> FEATURE:
<221> NAME/KEY: CDS
<222> LOCATION: (1)...(1239)

<400> SEQUENCE: 2

```
atg gag cgc gcg ccg ccc gac ggg ctg atg aac gcg tcg ggc act ctg      48
Met Glu Arg Ala Pro Pro Asp Gly Leu Met Asn Ala Ser Gly Thr Leu
 1               5                  10                  15
```

```
gcc gga gag gcg gcg gct gca ggc ggg gcg cgc ggc ttc tcg gct gcc    96
Ala Gly Glu Ala Ala Ala Ala Gly Gly Ala Arg Gly Phe Ser Ala Ala
         20                  25                  30 tgg acc gct gtc ctg gct gcg ctc atg gcg ctg ctc atc gtg gcc aca   144
Trp Thr Ala Val Leu Ala Ala Leu Met Ala Leu Leu Ile Val Ala Thr
     35                  40                  45 gta ctg ggc aac gcg ctg gtc atg ctc gcc ttc gtg gcg gat tcg agc   192
Val Leu Gly Asn Ala Leu Val Met Leu Ala Phe Val Ala Asp Ser Ser
 50                  55                  60 ctc cgc acc cag aac aac ttc ttt ctg ctc aac ctc gcc atc tcc gac   240
Leu Arg Thr Gln Asn Asn Phe Phe Leu Leu Asn Leu Ala Ile Ser Asp
 65                  70                  75                  80 ttc ctc gtg ggt gcc ttc tgc atc cca ttg tac gta ccc tat gtg ctg   288
Phe Leu Val Gly Ala Phe Cys Ile Pro Leu Tyr Val Pro Tyr Val Leu
                 85                  90                  95 acc ggc cgt tgg acc ttc ggc cgg ggc ctc tgc aag ctg tgg ctg gtg   336
Thr Gly Arg Trp Thr Phe Gly Arg Gly Leu Cys Lys Leu Trp Leu Val
             100                 105                 110 gta gac tac cta ctg tgt gcc tcc tcg gtc ttc aac atc gta ctc atc   384
Val Asp Tyr Leu Leu Cys Ala Ser Ser Val Phe Asn Ile Val Leu Ile
         115                 120                 125 agc tat gac cga ttc ctg tca gtc act cga gct gtc tcc tac agg gcc   432
Ser Tyr Asp Arg Phe Leu Ser Val Thr Arg Ala Val Ser Tyr Arg Ala
 130                 135                 140 cag cag ggg gac acg aga cgg gcc gtt cgg aag atg gca ctg gtg tgg   480
Gln Gln Gly Asp Thr Arg Arg Ala Val Arg Lys Met Ala Leu Val Trp
145                 150                 155                 160 gtg ctg gcc ttc ctg ctg tat ggg cct gcc atc ctg agt tgg gag tac   528
Val Leu Ala Phe Leu Leu Tyr Gly Pro Ala Ile Leu Ser Trp Glu Tyr
                 165                 170                 175 ctg tct ggt ggc agt tcc atc ccc gag ggc cac tgc tat gct gag ttc   576
Leu Ser Gly Gly Ser Ser Ile Pro Glu Gly His Cys Tyr Ala Glu Phe
             180                 185                 190 ttc tac aac tgg tac ttt ctc atc acg gcc tcc acc ctc gag ttc ttc   624
Phe Tyr Asn Trp Tyr Phe Leu Ile Thr Ala Ser Thr Leu Glu Phe Phe
         195                 200                 205 acg ccc ttc ctc agc gtt acc ttc ttc aac ctc agc atc tac ctg aac   672
Thr Pro Phe Leu Ser Val Thr Phe Phe Asn Leu Ser Ile Tyr Leu Asn
 210                 215                 220 atc cag agg cgc acc cgc ctt cgg ctt gat ggg ggc cgt gag gct ggc   720
Ile Gln Arg Arg Thr Arg Leu Arg Leu Asp Gly Gly Arg Glu Ala Gly
225                 230                 235                 240 cca gaa ccc cca cca gat gcc cag ccc tcg cca cct cca gct ccc ccc   768
Pro Glu Pro Pro Pro Asp Ala Gln Pro Ser Pro Pro Pro Ala Pro Pro
                 245                 250                 255 agc tgc tgg ggc tgc tgg cca aaa ggg cat ggc gag gcc atg ccg ttg   816
Ser Cys Trp Gly Cys Trp Pro Lys Gly His Gly Glu Ala Met Pro Leu
             260                 265                 270 cac agc tct ggc agc tcc tca agg ggc act gag agg cca cgc tca ctc   864
His Ser Ser Gly Ser Ser Ser Arg Gly Thr Glu Arg Pro Arg Ser Leu
         275                 280                 285 aaa agg ggc tcc aag cca tca gca tct tca gca tcc ctg gag aag cgc   912
Lys Arg Gly Ser Lys Pro Ser Ala Ser Ser Ala Ser Leu Glu Lys Arg
 290                 295                 300 atg aag atg gtg tcc cag agc atc acc cag cgc ttc cgg ctg tcg cgg   960
Met Lys Met Val Ser Gln Ser Ile Thr Gln Arg Phe Arg Leu Ser Arg
305                 310                 315                 320 gac aag aag gtg gcc aag tcg ctg gcc atc atc gtg agc atc ttt ggg  1008
Asp Lys Lys Val Ala Lys Ser Leu Ala Ile Ile Val Ser Ile Phe Gly
                 325                 330                 335
```

| | | | | | | | | | | | | |
|---|---|---|---|---|---|---|---|---|---|---|---|---|
| ctc | tgc | tgg | gcg | ccg | tac | acg | ctc | cta | atg | atc | atc | cga | gct | gct | tgc | 1056 |
| Leu | Cys | Trp | Ala | Pro | Tyr | Thr | Leu | Leu | Met | Ile | Ile | Arg | Ala | Ala | Cys | |
| | | | 340 | | | | | 345 | | | | | 350 | | | |

| cat | ggc | cgc | tgc | atc | ccc | gat | tac | tgg | tac | gag | acg | tcc | ttc | tgg | ctt | 1104 |
| His | Gly | Arg | Cys | Ile | Pro | Asp | Tyr | Trp | Tyr | Glu | Thr | Ser | Phe | Trp | Leu | |
| | | 355 | | | | | 360 | | | | | 365 | | | | |

| ctg | tgg | gcc | aac | tcg | gcc | gtc | aac | ccc | gtc | ctc | tac | cca | ctg | tgc | cac | 1152 |
| Leu | Trp | Ala | Asn | Ser | Ala | Val | Asn | Pro | Val | Leu | Tyr | Pro | Leu | Cys | His | |
| | 370 | | | | 375 | | | | | 380 | | | | | | |

| tac | agc | ttc | cgc | aga | gcc | ttc | acc | aag | ctc | ctc | tgc | ccc | cag | aag | ctc | 1200 |
| Tyr | Ser | Phe | Arg | Arg | Ala | Phe | Thr | Lys | Leu | Leu | Cys | Pro | Gln | Lys | Leu | |
| 385 | | | | 390 | | | | | 395 | | | | | 400 | | |

| aag | gtc | cag | ccc | cac | ggc | tcc | ctg | gag | cag | tgc | tgg | aag | | | | 1239 |
| Lys | Val | Gln | Pro | His | Gly | Ser | Leu | Glu | Gln | Cys | Trp | Lys | | | | |
| | | | | 405 | | | | | 410 | | | | | | | |

```
<210> SEQ ID NO 3
<211> LENGTH: 21
<212> TYPE: DNA
<213> ORGANISM: Artificial Sequence
<220> FEATURE:
<223> OTHER INFORMATION: artificially synthesized primer sequence
<220> FEATURE:
<221> NAME/KEY: misc_feature
<222> LOCATION: (1)...(21)
<223> OTHER INFORMATION: n = A,T,C or G

<400> SEQUENCE: 3
batngccaac ctbkccttct c                                                 21

<210> SEQ ID NO 4
<211> LENGTH: 20
<212> TYPE: DNA
<213> ORGANISM: Artificial Sequence
<220> FEATURE:
<223> OTHER INFORMATION: artificially synthesized primer sequence
<220> FEATURE:
<221> NAME/KEY: misc_feature
<222> LOCATION: (1)...(20)
<223> OTHER INFORMATION: n = A,T,C or G

<400> SEQUENCE: 4
ccataaaagn ngggttgac                                                    20

<210> SEQ ID NO 5
<211> LENGTH: 2700
<212> TYPE: DNA
<213> ORGANISM: Rattus norvegicus
<220> FEATURE:
<221> NAME/KEY: CDS
<222> LOCATION: (351)...(1589)
<220> FEATURE:
<221> NAME/KEY: misc_feature
<222> LOCATION: (1)...(2700)
<223> OTHER INFORMATION: n = A,T,C or G

<400> SEQUENCE: 5
aattcggcac gagcgggcag atcgcggggc gcactcggtt gcgcgctgag ctaggggtgc      60
accgacgcac cgcgggcgg  tggagctcgg ctttgctctc gctgcagcag ccgcgccgcc     120
cgccccactc cgctcagatt ccgacaccag ccccctctgg atcgccctcc tggactctag     180
cccgggctct tgctccgacc ccgcggacca tgctccgggc gccccccgga aaaccgggct     240
gggcgaagag ccggcaaaga ttaggctcac gagcggggc  cccacccggc cacccagctc     300
tccgcccgtg ccctgcccgg tgtccccgag ccgtgtgagc ctgctgggcc atg gag       356
```

-continued

```
                                              Met Glu
                                              1
cgc gcg ccg ccc gac ggg ctg atg aac gcg tcg ggc act ctg gcc gga    404
Arg Ala Pro Pro Asp Gly Leu Met Asn Ala Ser Gly Thr Leu Ala Gly
     5                  10                  15 gag gcg gcg gct gca ggc ggg gcg cgc ggc ttc tcg gct gcc tgg acc    452
Glu Ala Ala Ala Ala Gly Gly Ala Arg Gly Phe Ser Ala Ala Trp Thr
         20                  25                  30 gct gtc ctg gct gcg ctc atg gcg ctg ctc atc gtg gcc aca gta ctg    500
Ala Val Leu Ala Ala Leu Met Ala Leu Leu Ile Val Ala Thr Val Leu
 35                  40                  45                  50 ggc aac gcg ctg gtc atg ctc gcc ttc gtg gcg gat tcg agc ctc cgc    548
Gly Asn Ala Leu Val Met Leu Ala Phe Val Ala Asp Ser Ser Leu Arg
                 55                  60                  65 acc cag aac aac ttt ttt ctg ctc aac ctc gcc atc tcc gac ttc ctc    596
Thr Gln Asn Asn Phe Phe Leu Leu Asn Leu Ala Ile Ser Asp Phe Leu
             70                  75                  80 gtg ggt gcc ttc tgc atc cca ttg tac gta ccc tat gtg ctg acc ggc    644
Val Gly Ala Phe Cys Ile Pro Leu Tyr Val Pro Tyr Val Leu Thr Gly
         85                  90                  95 cgt tgg acc ttc ggc cgg ggc ctc tgc aag ctg tgg ctg gtg gta gac    692
Arg Trp Thr Phe Gly Arg Gly Leu Cys Lys Leu Trp Leu Val Val Asp
100                 105                 110 tac cta ctg tgt gcc tcc tcg gtc ttc aac atc gta ctc atc agc tat    740
Tyr Leu Leu Cys Ala Ser Ser Val Phe Asn Ile Val Leu Ile Ser Tyr
115                 120                 125                 130 gac cga ttc ctg tca gtc act cga gct gtc tcc tac agg gcc cag cag    788
Asp Arg Phe Leu Ser Val Thr Arg Ala Val Ser Tyr Arg Ala Gln Gln
                135                 140                 145 ggg gac acg aga cgg gcc gtt cgg aag atg gca ctg gtg tgg gtg ctg    836
Gly Asp Thr Arg Arg Ala Val Arg Lys Met Ala Leu Val Trp Val Leu
            150                 155                 160 gcc ttc ctg ctg tat ggg cct gcc atc ctg agt tgg gag tac ctg tct    884
Ala Phe Leu Leu Tyr Gly Pro Ala Ile Leu Ser Trp Glu Tyr Leu Ser
        165                 170                 175 ggt ggc agt tcc atc ccc gag ggc cac tgc tat gct gag ttc ttc tac    932
Gly Gly Ser Ser Ile Pro Glu Gly His Cys Tyr Ala Glu Phe Phe Tyr
    180                 185                 190 aac tgg tac ttt ctc atc acg gcc tcc acc ctc gag ttc ttc acg ccc    980
Asn Trp Tyr Phe Leu Ile Thr Ala Ser Thr Leu Glu Phe Phe Thr Pro
195                 200                 205                 210 ttc ctc agc gtt acc ttc ttc aac ctc agc atc tac ctg aac atc cag   1028
Phe Leu Ser Val Thr Phe Phe Asn Leu Ser Ile Tyr Leu Asn Ile Gln
                215                 220                 225 agg cgc acc cgc ctt cgg ctt gat ggg ggc cgt gag gct ggc cca gaa   1076
Arg Arg Thr Arg Leu Arg Leu Asp Gly Gly Arg Glu Ala Gly Pro Glu
            230                 235                 240 ccc cca cca gat gcc cag ccc tcg cca cct cca gct ccc ccc agc tgc   1124
Pro Pro Pro Asp Ala Gln Pro Ser Pro Pro Pro Ala Pro Pro Ser Cys
        245                 250                 255 tgg ggc tgc tgg cca aaa ggg cat ggc gag gcc atg ccg ttg cac agc   1172
Trp Gly Cys Trp Pro Lys Gly His Gly Glu Ala Met Pro Leu His Ser
    260                 265                 270 tct ggc agc tcc tca agg ggc act gag agg cca cgc tca ctc aaa agg   1220
Ser Gly Ser Ser Ser Arg Gly Thr Glu Arg Pro Arg Ser Leu Lys Arg
275                 280                 285                 290 ggc tcc aag cca tca gca tct tca gca tcc ctg gag aag cgc atg aag   1268
Gly Ser Lys Pro Ser Ala Ser Ser Ala Ser Leu Glu Lys Arg Met Lys
                295                 300                 305
```

```
atg gtg tcc cag agc atc acc cag cgc ttc cgg ctg tcg cgg gac aag    1316
Met Val Ser Gln Ser Ile Thr Gln Arg Phe Arg Leu Ser Arg Asp Lys
            310                 315                 320 aag gtg gcc aag tcg ctg gcc atc atc gtg agc atc ttt ggg ctc tgc    1364
Lys Val Ala Lys Ser Leu Ala Ile Ile Val Ser Ile Phe Gly Leu Cys
                325                 330                 335 tgg gcg ccg tac acg ctc cta atg atc atc cga gct gct tgc cat ggc    1412
Trp Ala Pro Tyr Thr Leu Leu Met Ile Ile Arg Ala Ala Cys His Gly
        340                 345                 350 cgc tgc atc ccc gat tac tgg tac gag acg tcc ttc tgg ctt ctg tgg    1460
Arg Cys Ile Pro Asp Tyr Trp Tyr Glu Thr Ser Phe Trp Leu Leu Trp
355                 360                 365                 370 gcc aac tcg gcc gtc aac ccc gtc ctc tac cca ctg tgc cac tac agc    1508
Ala Asn Ser Ala Val Asn Pro Val Leu Tyr Pro Leu Cys His Tyr Ser
                375                 380                 385 ttc cgc aga gcc ttc acc aag ctc ctc tgc ccc cag aag ctc aag gtc    1556
Phe Arg Arg Ala Phe Thr Lys Leu Leu Cys Pro Gln Lys Leu Lys Val
        390                 395                 400 cag ccc cac ggc tcc ctg gag cag tgc tgg aag tgagcagctg ccccacccctt  1609
Gln Pro His Gly Ser Leu Glu Gln Cys Trp Lys
            405                 410 ctgaggccag gcccttgtac ttgtttgagt gggcagccgg agcgtgggcg gggccctggt   1669
ccatgctccg ctccaaatgc catggcggcc tcttagatca tcaaccccgc agtggggtag   1729
catggcaggt gggccaagag ccctagttgg tggagctaga gtgtgctggt tagctctgcc   1789
gccacattct ccttcaccac acagaagaga caatccagga gtcccaggca tgccttccac   1849
ctacacacac acacacacac acacacacac acacaccaca gtgcagtgcc agtgatgtcc   1909
ccttttgcat atttagtggt tggtgtcctc cctaatgcaa acctcggtgt gtgctcccgg   1969
ctccggccct ggcaatgcgt gcgtgcgccc tgcatgtgct cacacccgcc acacacccgc   2029
ccgccacaca cttgcaacac ctcctctctc ccagaagagc tggggacgat gccctttgct   2089
gccactgtct cttgcttaat cccagagcct ggctccttat ccccactctc ccttcaact    2149 ctgccccaca aagtgtcgag cgcctcggga aacttgaagc ttctctgctc cttccactct   2209
ggatgttttc aggaagatgg aggagaagaa aacacgtctg tgaacttgat gttccttgga   2269
tgtttaatca agagagacaa aattgccgag gagctcgggg ctggattggc aggtgtgggc   2329
tcccacgccc tcctccctca gtgctgcagc ttccggctga gccgcgccag ctgcttctgc   2389
ctgccccgcc cccaggcttg ggacgatggc cctgccctgc ttgccccgtc tgtacaatca   2449
gaatttgggg gtgggtggtt atggggtaga gcggctcttc actgtgccct aaaggtcctg   2509
aggctcacag gacagtcagc aggagagcag gcaggcccgc gacacctggg aggaatgctt   2569
tgcctcgtcc tgtgtactca cctcaggctt ctgcatgctc tgctgccctt gtgccctggt   2629
gtgctgcctc tgccaatgtg aaaacacaat aaagtgtatt tttttacgga aaaaaaana    2689 aaaaaaaaaa a                                                        2700

<210> SEQ ID NO 6
<211> LENGTH: 29
<212> TYPE: DNA
<213> ORGANISM: Artificial Sequence
<220> FEATURE:
<223> OTHER INFORMATION: artificially synthesized primer sequence

<400> SEQUENCE: 6
cgaggatccg tgaggctccg gtgcccgtc                                      29
```

```
<210> SEQ ID NO 7
<211> LENGTH: 32
<212> TYPE: DNA
<213> ORGANISM: Artificial Sequence
<220> FEATURE:
<223> OTHER INFORMATION: artificially synthesized primer sequence

<400> SEQUENCE: 7
cgggtaagct tcacgacacc tgaaatggaa ga                                      32

<210> SEQ ID NO 8
<211> LENGTH: 25
<212> TYPE: DNA
<213> ORGANISM: Artificial Sequence
<220> FEATURE:
<223> OTHER INFORMATION: artificially synthesized primer sequence

<400> SEQUENCE: 8
ccttctgcat cccattgtac gtacc                                              25

<210> SEQ ID NO 9
<211> LENGTH: 21
<212> TYPE: DNA
<213> ORGANISM: Artificial Sequence
<220> FEATURE:
<223> OTHER INFORMATION: artificially synthesized primer sequence

<400> SEQUENCE: 9
cttccgccgg gccttcacca a                                                  21

<210> SEQ ID NO 10
<211> LENGTH: 20
<212> TYPE: DNA
<213> ORGANISM: Artificial Sequence
<220> FEATURE:
<223> OTHER INFORMATION: artificially synthesized primer sequence

<400> SEQUENCE: 10
acagacacgg cggggctcac                                                    20

<210> SEQ ID NO 11
<211> LENGTH: 1350
<212> TYPE: DNA
<213> ORGANISM: Homo sapiens
<220> FEATURE:
<221> NAME/KEY: exon
<222> LOCATION: (280)...(557)
<220> FEATURE:
<221> NAME/KEY: misc_feature
<222> LOCATION: (1)...(1350)
<223> OTHER INFORMATION: n = A,T,C or G

<400> SEQUENCE: 11
gcactcggct gcgcgttgcn tccggctgca cggtcgcacc ggcagcggct caggctccgg         60
ctcctctccc gctgcagcag ccgcgctgcc ggccccactg ggctcggatc cggcccggc         120 ccctcggca ccgcctgctc tggccccggc cccggccccg cggaccatgc gctgggcgcc         180
cccaggggaa cccgacccgg ccaagggccc gcaaagacga ggctcccggg ccggggcccc        240
tcccggccgc ccagctctcg gccggcgccc tgccccgcgt cccggagccg cgtgagcctg        300
cggggccatg gagcgcgcgc cgcccgacgg gcgctgaac gcttcggggg cgctggcggg         360
cgaggcggcg gcggcgggcg gggcgcgcgg cttctcggca gcctggaccg cggtgctggc        420
cgcgctcatg gcgctgctca tcgtggccac ggtgctgggc aacgcgctgg tcatgctcgc        480
cttcgtggcc gactcgagcc tccgcaccca gaacaacttc ttcctgctca acctcgccat       540
```

```
ctccgacttc ctcgtcggta atccccagc ccctggccgc tggggaccca ggggcgccca        600
gcgtggccgg gccagcgggg actggaacac ggacctgggt ggctcccgca ggcacacgcc        660
ccaccagggg acccgcctg gaagggggc gtccggagcc catggggtgg ggggcacagg         720
cgaagttcct tgccactcag gcctcgggac agggctggg gagagatgtc cccgggaagg         780
gacacgggca ctgggcgagg cgcaaggcgc aaaggcagcg gtgcagctc tggctcctgc         840 gctgtagcca aacaaaggct gctgcggact taggacgcgc ggagggcgca gtgggcggt         900 ttagagaagg tctgggggag gggacatgga aggggattt ttagagctgt gttgggggaa         960
gggacggtgg ggaaggtggg ggttggggga gacgctcgga ggagcgtgct ctcacgtgtc        1020
caggctctgc tgccggctgg ggggcggggc acgcggaggg ggctgagcg ccagacacct         1080 gttgggggctg tgaggtgcgt ctcccagacg ctccaagccc gcttggcagt agtagtagcg       1140
gctggcggct ggcggctgca accaagtgcc ctttcagcca ggagaaaggc tttctccttg        1200
tctaagctga gaccgagggt tgtccagcgc cagggtaggg gctggagtcc agcggggag         1260 gggagaagga aattgtcttc tttcctcctt tgagggctgg gagggctgga cagaagtcca        1320
gggaatcccg actccaggct ctcgggggtc                                         1350

<210> SEQ ID NO 12
<211> LENGTH: 448
<212> TYPE: DNA
<213> ORGANISM: Homo sapiens
<220> FEATURE:
<221> NAME/KEY: exon
<222> LOCATION: (259)...(425)

<400> SEQUENCE: 12
gagctcccca tgcctggatc atccctcctg cccccaggcc caggggacac agatagtgct         60
gggagctatg tggggggtgaa ggctggcggc agggcagagt ttgtggctga caccaggtgg       120
aggggtggta agatgaggat ggctagttcc agaaaagcag ccaccatgtg accccaggtc       180
ccgccggtgt ctgcgcttag gtccgtctgt cccctggccc ctggctgcat ggtcccactg       240
tggccctact ccccacaggc gccttctgca tcccactgta tgtaccctac gtgctgacag       300
gccgctggac cttcggccgg ggcctctgca agctgtggct ggtagtggac tacctgctgt       360
gcacctcctc tgccttcaac atcgtgctca tcagctacga ccgcttcctg tcggtcaccc       420
gagcggtgag tcctgggctg cggagctc                                          448

<210> SEQ ID NO 13
<211> LENGTH: 1893
<212> TYPE: DNA
<213> ORGANISM: Homo sapiens
<220> FEATURE:
<221> NAME/KEY: exon
<222> LOCATION: (293)...(1209)

<400> SEQUENCE: 13
gagctcacag ctggtagggg gtggtaaaca ggcagcctag cagagagtga gggttcaggt         60
tggtcccagg gagcttctga ggctctcact gagtgtggca gggcaccagt ccgggacccc       120
agtggggagg gttagaggaa gggaggggaa agagggaggg aggaggaca ggaggggaaa        180 ggaggagcat tgctgctgag ggaagggccc acatagggc ccacaggcta cggggcgca         240 cccagcccaa tattccttcc gccccgcccc tgaccagcct gcccttctgc aggtctcata       300
ccgggcccag cagggtgaca cgcggcgggc agtgcggaag atgctgctgg tgtgggtgct       360
```

-continued

```
ggccttcctg ctgtacggac cagccatcct gagctgggag tacctgtccg ggggcagctc      420
catccccgag ggccactgct atgccgagtt cttctacaac tggtacttcc tcatcacggc      480
ttccaccctg gagttcttta cgccttcct cagcgtcacc ttctttaacc tcagcatcta      540
cctgaacatc cagaggcgca cccgcctccg gctggatggg gctcgagagg cagccggccc      600
cgagccccct cccgaggccc agccctcacc accccaccg cctggctgct ggggctgctg      660
gcagaagggg cacggggagg ccatgccgct gcacaggtat ggggtgggtg aggcggccgt      720
aggcgctgag gccggggagg cgaccctcgg gggtggcggt ggggcggct ccgtggcttc      780 acccacctcc agctccggca gctcctcgag ggcactgag aggccgcgct cactcaagag       840
gggctccaag ccatcggcgt cctcggcctc actggagaag cgcatgaaga tggtgtccca     900
gagcttcacc cagcgctttc ggctgtctcg gacaggaaa gtggccaagt cgctggccgt      960
catcgtgagc atctttgggc tctgctgggc cccatacacg ctgctgatga tcatccgggc     1020
cgcctgccat ggccactgcg tccctgacta ctggtacgaa acctccttct ggctcctgtg     1080
ggccaactcg gctgtcaacc ctgtcctcta ccctctgtgc caccacagct ccgccgggc      1140 cttcaccaag ctgctctgcc cccagaagct caaaatccag ccccacagct ccctggagca     1200
ctgctggaag tgagtggccc accagagcct ccctcagcca cgcctctctc agcccaggtc     1260
tcctgggcat ctggccctgc tgcccctac ccggctcgtt ccccaggggg tgagccccgc      1320
cgtgtctgtg gccctctctt aatgccacgg cagccaccct gccatggagg cgccttcctg     1380
ggttggccag agggcccctc actggctgga ctggaggctg ggtggccggc cctgccccc       1440 acattctggc tccaccggga gggacagtct ggaggtccca gacatgctgc ccacccctg      1500 ctggtgccca cccttcgcag ttactggttg gtgttcttcc caaagcaagc acctgggtgt     1560
gctccaggct tcctgcccta gcagtttgcc tctgcacgtg cacacacctg cacacccctg    1620
cacacacctg cacaccgtcc ctctccccgg acaagcccag gacactgcct ttgctgcctt     1680
ctgtctcttg cataagcctc aggcctggcc ctttcacccc tcttcccacc aactctctct    1740
gcccccaaaa gtgtcaaggg gccctaggaa cctcgaagct gttctctgct tttccattct     1800
gggtgttttc agaaagatga agaagaaaac atgtctgtga acttgatgtt cctgggatgt     1860
ttaatcaaga gagacaaaat tgctgaggag ctc                                  1893
```

<210> SEQ ID NO 14
<211> LENGTH: 20
<212> TYPE: DNA
<213> ORGANISM: Artificial Sequence
<220> FEATURE:
<223> OTHER INFORMATION: artificially synthesized primer sequence

<400> SEQUENCE: 14

```
tgaacgcttc gggggcgctg                                                   20
```

<210> SEQ ID NO 15
<211> LENGTH: 21
<212> TYPE: DNA
<213> ORGANISM: Artificial Sequence
<220> FEATURE:
<223> OTHER INFORMATION: artificially synthesized primer sequence

<400> SEQUENCE: 15

```
gagatggcga ggttgagcag g                                                 21
```

<210> SEQ ID NO 16
<211> LENGTH: 20

```
<212> TYPE: DNA
<213> ORGANISM: Artificial Sequence
<220> FEATURE:
<223> OTHER INFORMATION: artificially synthesized primer sequence

<400> SEQUENCE: 16
ggctccaagc catcggcgtc                                               20

<210> SEQ ID NO 17
<211> LENGTH: 20
<212> TYPE: DNA
<213> ORGANISM: Artificial Sequence
<220> FEATURE:
<223> OTHER INFORMATION: artificially synthesized primer sequence

<400> SEQUENCE: 17
ctcacttcca gcagtgctcc                                               20

<210> SEQ ID NO 18
<211> LENGTH: 20
<212> TYPE: DNA
<213> ORGANISM: Artificial Sequence
<220> FEATURE:
<223> OTHER INFORMATION: artificially synthesized primer sequence

<400> SEQUENCE: 18
gcctccgcac ccagaacaac                                               20

<210> SEQ ID NO 19
<211> LENGTH: 19
<212> TYPE: DNA
<213> ORGANISM: Artificial Sequence
<220> FEATURE:
<223> OTHER INFORMATION: artificially synthesized primer sequence

<400> SEQUENCE: 19
tgcgcctctg gatgttcag                                                19

<210> SEQ ID NO 20
<211> LENGTH: 453
<212> TYPE: PRT
<213> ORGANISM: Homo sapiens

<400> SEQUENCE: 20

Met Glu Arg Ala Pro Pro Asp Gly Pro Leu Asn Ala Ser Gly Ala Leu
  1               5                  10                  15

Ala Gly Glu Ala Ala Ala Ala Gly Gly Ala Arg Gly Phe Ser Ala Ala
             20                  25                  30

Trp Thr Ala Val Leu Ala Ala Leu Met Ala Leu Leu Ile Val Ala Thr
         35                  40                  45

Val Leu Gly Asn Ala Leu Val Met Leu Ala Phe Val Ala Asp Ser Ser
     50                  55                  60

Leu Arg Thr Gln Asn Asn Phe Phe Leu Leu Asn Leu Ala Ile Ser Asp
 65                  70                  75                  80

Phe Leu Val Gly Ala Phe Cys Ile Pro Leu Tyr Val Pro Tyr Val Leu
                 85                  90                  95

Thr Gly Arg Trp Thr Phe Gly Arg Gly Leu Cys Lys Leu Trp Leu Val
            100                 105                 110

Val Asp Tyr Leu Leu Cys Thr Ser Ser Ala Phe Asn Ile Val Leu Ile
        115                 120                 125

Ser Tyr Asp Arg Phe Leu Ser Val Thr Arg Ala Val Ser Tyr Arg Ala
    130                 135                 140
```

```
Gln Gln Gly Asp Thr Arg Arg Ala Val Arg Lys Met Leu Leu Val Trp
145                 150                 155                 160

Val Leu Ala Phe Leu Leu Tyr Gly Pro Ala Ile Leu Ser Trp Glu Tyr
            165                 170                 175

Leu Ser Gly Gly Ser Ser Ile Pro Glu Gly His Cys Tyr Ala Glu Phe
        180                 185                 190

Phe Tyr Asn Trp Tyr Phe Leu Ile Thr Ala Ser Thr Leu Glu Phe Phe
        195                 200                 205

Thr Pro Phe Leu Ser Val Thr Phe Phe Asn Leu Ser Ile Tyr Leu Asn
    210                 215                 220

Ile Gln Arg Arg Thr Arg Leu Arg Leu Asp Gly Ala Arg Glu Ala Ala
225                 230                 235                 240

Gly Pro Glu Pro Pro Glu Ala Gln Pro Ser Pro Pro Pro Pro Pro Pro
                245                 250                 255

Gly Cys Trp Gly Cys Trp Gln Lys Gly His Gly Glu Ala Met Pro Leu
            260                 265                 270

His Arg Tyr Gly Val Gly Glu Ala Ala Val Gly Ala Glu Ala Gly Glu
        275                 280                 285

Ala Thr Leu Gly Gly Gly Gly Gly Gly Ser Val Ala Ser Pro Thr
    290                 295                 300

Ser Ser Ser Gly Ser Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
                325                 330                 335

Met Lys Met Val Ser Gln Ser Phe Thr Gln Arg Phe Arg Leu Ser Arg
            340                 345                 350

Asp Arg Lys Val Ala Lys Ser Leu Ala Val Ile Val Ser Ile Phe Gly
        355                 360                 365

Leu Cys Trp Ala Pro Tyr Thr Leu Leu Met Ile Ile Arg Ala Ala Cys
    370                 375                 380

His Gly His Cys Val Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
                405                 410                 415

His Ser Phe Arg Arg Ala Phe Thr Lys Leu Leu Cys Pro Gln Lys Leu
            420                 425                 430

Lys Ile Gln Pro His Ser Ser Leu Glu His Cys Trp Lys Lys Met Lys
        435                 440                 445

Lys Lys Thr Cys Leu
    450

<210> SEQ ID NO 21
<211> LENGTH: 2050
<212> TYPE: DNA
<213> ORGANISM: Homo sapiens
<220> FEATURE:
<221> NAME/KEY: CDS
<222> LOCATION: (271)...(1629)

<400> SEQUENCE: 21
agagatgtag ggcgcccctt ttagctgcgc acagaacgaa agaactcgtt ttttctttaa      60
gtgagtgtgc ttgggtgacg cttagggcgc cctccgcagt gcgcgcagga aagcgcactg     120
aggctgcgga ggcagagctg catgctgggt gcgggaagag gtgggctccg tcgcggagtc     180
gctgagtccg tgcccttta gttagttctg cagtctagta tggtccccat ttgcccttcc     240
```

-continued

```
actcccggag ccgcgtgagc ctgcggggcc atg gag cgc gcg ccg ccc gac ggg      294
                                Met Glu Arg Ala Pro Pro Asp Gly
                                 1               5 ccg ctg aac gct tcg ggg gcg ctg gcg ggc gag gcg gcg gcg ggc           342
Pro Leu Asn Ala Ser Gly Ala Leu Ala Gly Glu Ala Ala Ala Gly
         10                  15                  20 ggg gcg cgc ggc ttc tcg gca gcc tgg acc gcg gtg ctg gcc gcg ctc       390
Gly Ala Arg Gly Phe Ser Ala Ala Trp Thr Ala Val Leu Ala Ala Leu
 25                  30                  35                  40 atg gcg ctg ctc atc gtg gcc acg gtg ctg ggc aac gcg ctg gtc atg       438
Met Ala Leu Leu Ile Val Ala Thr Val Leu Gly Asn Ala Leu Val Met
                 45                  50                  55 ctc gcc ttc gtg gcc gac tcg agc ctc cgc acc cag aac aac ttc ttc       486
Leu Ala Phe Val Ala Asp Ser Ser Leu Arg Thr Gln Asn Asn Phe Phe
             60                  65                  70 ctg ctc aac ctc gcc atc tcc gac ttc ctc gtc ggc gcc ttc tgc atc       534
Leu Leu Asn Leu Ala Ile Ser Asp Phe Leu Val Gly Ala Phe Cys Ile
             75                  80                  85 cca ctg tat gta ccc tac gtg ctg aca ggc cgc tgg acc ttc ggc cgg       582
Pro Leu Tyr Val Pro Tyr Val Leu Thr Gly Arg Trp Thr Phe Gly Arg
         90                  95                 100 ggc ctc tgc aag ctg tgg ctg gta gtg gac tac ctg ctg tgc acc tcc       630
Gly Leu Cys Lys Leu Trp Leu Val Val Asp Tyr Leu Leu Cys Thr Ser
105                 110                 115                 120 tct gcc ttc aac atc gtg ctc atc agc tac gac cgc ttc ctg tcg gtc       678
Ser Ala Phe Asn Ile Val Leu Ile Ser Tyr Asp Arg Phe Leu Ser Val
                125                 130                 135 acc cga gcg gtc tca tac cgg gcc cag cag ggt gac acg cgg cgg gca       726
Thr Arg Ala Val Ser Tyr Arg Ala Gln Gln Gly Asp Thr Arg Arg Ala
            140                 145                 150 gtg cgg aag atg ctg ctg gtg tgg gtg ctg gcc ttc ctg ctg tac gga       774
Val Arg Lys Met Leu Leu Val Trp Val Leu Ala Phe Leu Leu Tyr Gly
            155                 160                 165 cca gcc atc ctg agc tgg gag tac ctg tcc ggg ggc agc tcc atc ccc       822
Pro Ala Ile Leu Ser Trp Glu Tyr Leu Ser Gly Gly Ser Ser Ile Pro
        170                 175                 180 gag ggc cac tgc tat gcc gag ttc ttc tac aac tgg tac ttc ctc atc       870
Glu Gly His Cys Tyr Ala Glu Phe Phe Tyr Asn Trp Tyr Phe Leu Ile
185                 190                 195                 200 acg gct tcc acc ctg gag ttc ttt acg ccc ttc ctc agc gtc acc ttc       918
Thr Ala Ser Thr Leu Glu Phe Phe Thr Pro Phe Leu Ser Val Thr Phe
                205                 210                 215 ttt aac ctc agc atc tac ctg aac atc cag agg cgc acc cgc ctc cgg       966
Phe Asn Leu Ser Ile Tyr Leu Asn Ile Gln Arg Arg Thr Arg Leu Arg
            220                 225                 230 ctg gat ggg gct cga gag gca gcc ggc ccc gag ccc cct ccc gag gcc      1014
Leu Asp Gly Ala Arg Glu Ala Ala Gly Pro Glu Pro Pro Pro Glu Ala
            235                 240                 245 cag ccc tca cca ccc cca ccg cct ggc tgc tgg ggc tgc tgg cag aag      1062
Gln Pro Ser Pro Pro Pro Pro Pro Gly Cys Trp Gly Cys Trp Gln Lys
        250                 255                 260 ggg cac ggg gag gcc atg ccg ctg cac agg tat ggg gtg ggt gag gcg      1110
Gly His Gly Glu Ala Met Pro Leu His Arg Tyr Gly Val Gly Glu Ala
265                 270                 275                 280 gcc gta ggc gct gag gcc ggg gag gcg acc ctc ggg ggt ggc ggt ggg      1158
Ala Val Gly Ala Glu Ala Gly Glu Ala Thr Leu Gly Gly Gly Gly Gly
                285                 290                 295 ggc ggc tcc gtg gct tca ccc acc tcc agc tcc ggc agc tcc tcg agg      1206
Gly Gly Ser Val Ala Ser Pro Thr Ser Ser Gly Ser Ser Ser Arg
```

```
                    300             305             310
ggc act gag agg ccg cgc tca ctc aag agg ggc tcc aag ccg tcg gcg    1254
Gly Thr Glu Arg Pro Arg Ser Leu Lys Arg Gly Ser Lys Pro Ser Ala
            315                 320                 325 tcc tcg gcc tcg ctg gag aag cgc atg aag atg gtg tcc cag agc ttc    1302
Ser Ser Ala Ser Leu Glu Lys Arg Met Lys Met Val Ser Gln Ser Phe
        330                 335                 340 acc cag cgc ttt cgg ctg tct cgg gac agg aaa gtg gcc aag tcg ctg    1350
Thr Gln Arg Phe Arg Leu Ser Arg Asp Arg Lys Val Ala Lys Ser Leu
345                 350                 355                 360 gcc gtc atc gtg agc atc ttt ggg ctc tgc tgg gcc cca tac acg ctg    1398
Ala Val Ile Val Ser Ile Phe Gly Leu Cys Trp Ala Pro Tyr Thr Leu
                365                 370                 375 ctg atg atc atc cgg gcc gcc tgc cat ggc cac tgc gtc cct gac tac    1446
Leu Met Ile Ile Arg Ala Ala Cys His Gly His Cys Val Pro Asp Tyr
            380                 385                 390 tgg tac gaa acc tcc ttc tgg ctc ctg tgg gcc aac tcg gct gtc aac    1494
Trp Tyr Glu Thr Ser Phe Trp Leu Leu Trp Ala Asn Ser Ala Val Asn
        395                 400                 405 cct gtc ctc tac cct ctg tgc cac cac agc ttc cgc cgg gcc ttc acc    1542
Pro Val Leu Tyr Pro Leu Cys His His Ser Phe Arg Arg Ala Phe Thr
    410                 415                 420 aag ctg ctc tgc ccc cag aag ctc aaa atc cag ccc cac agc tcc ctg    1590
Lys Leu Leu Cys Pro Gln Lys Leu Lys Ile Gln Pro His Ser Ser Leu
425                 430                 435                 440 gag cac tgc tgg aaa aag atg aag aag aaa aca tgt ctg tgaacttgat     1639
Glu His Cys Trp Lys Lys Met Lys Lys Lys Thr Cys Leu
                445                 450 gttcctggga tgtttaatca agagagacaa aattgctgag gagctcaggg ctggattggc  1699
aggtgtgggc tcccacgccc tcctccctcc gctaaggctt ccggctgagc tgtgccagct  1759
gcttctgccc acccegccte tgggctcaca ccagccctgg tggccaagcc tgccccggcc  1819
actctgtttg ctcacccagg acctctgggg gttgttggga ggaggggcc cggctgggcc   1879 cgagggtccc aaggcgtgca ggggcggtcc agaggaggtg cccgggcagg ggccgcttcg  1939
ccatgtgctg tgcacccgtg ccacgcgctc tgcatgctcc tctgcctgtg cccgctgcgc  1999
tgccctgcaa accgtgaggt cacaataaag tgtatttttt tattggtgct g          2050
```

<210> SEQ ID NO 22
<211> LENGTH: 20
<212> TYPE: DNA
<213> ORGANISM: Artificial Sequence
<220> FEATURE:
<223> OTHER INFORMATION: artificially synthesized primer sequence
<220> FEATURE:
<221> NAME/KEY: misc_feature
<222> LOCATION: (1)...(20)
<223> OTHER INFORMATION: n = A,T,C or G

<400> SEQUENCE: 22
tgcatcccat tgtacgtncc                                              20

<210> SEQ ID NO 23
<211> LENGTH: 20
<212> TYPE: DNA
<213> ORGANISM: Artificial Sequence
<220> FEATURE:
<223> OTHER INFORMATION: artificially synthesized primer sequence
<220> FEATURE:
<221> NAME/KEY: misc_feature
<222> LOCATION: (1)...(20)
<223> OTHER INFORMATION: n = A,T,C or G

<400> SEQUENCE: 23
atcattagga gcgtgtangg                                           20

<210> SEQ ID NO 24
<211> LENGTH: 20
<212> TYPE: DNA
<213> ORGANISM: Artificial Sequence
<220> FEATURE:
<223> OTHER INFORMATION: artificially synthesized primer sequence

<400> SEQUENCE: 24
tgctctggga caccatcttc                                           20

<210> SEQ ID NO 25
<211> LENGTH: 445
<212> TYPE: PRT
<213> ORGANISM: Rattus norvegicus

<400> SEQUENCE: 25

Met Glu Arg Ala Pro Pro Asp Gly Leu Met Asn Ala Ser Gly Thr Leu
 1               5                  10                  15

Ala Gly Glu Ala Ala Ala Gly Gly Ala Arg Gly Phe Ser Ala Ala
            20                  25                  30

Trp Thr Ala Val Leu Ala Ala Leu Met Ala Leu Leu Ile Val Ala Thr
    35                  40                  45

Val Leu Gly Asn Ala Leu Val Met Leu Ala Phe Val Ala Asp Ser Ser
    50                  55                  60

Leu Arg Thr Gln Asn Asn Phe Phe Leu Leu Asn Leu Ala Ile Ser Asp
65                  70                  75                  80

Phe Leu Val Gly Ala Phe Cys Ile Pro Leu Tyr Val Pro Tyr Val Leu
                85                  90                  95

Thr Gly Arg Trp Thr Phe Gly Arg Gly Leu Cys Lys Leu Trp Leu Val
            100                 105                 110

Val Asp Tyr Leu Leu Cys Ala Ser Ser Val Phe Asn Ile Val Leu Ile
        115                 120                 125

Ser Tyr Asp Arg Phe Leu Ser Val Thr Arg Ala Val Ser Tyr Arg Ala
    130                 135                 140

Gln Gln Gly Asp Thr Arg Arg Ala Val Arg Lys Met Ala Leu Val Trp
145                 150                 155                 160

Val Leu Ala Phe Leu Leu Tyr Gly Pro Ala Ile Leu Ser Trp Glu Tyr
                165                 170                 175

Leu Ser Gly Gly Ser Ser Ile Pro Glu Gly His Cys Tyr Ala Glu Phe
            180                 185                 190

Phe Tyr Asn Trp Tyr Phe Leu Ile Thr Ala Ser Thr Leu Glu Phe Phe
        195                 200                 205

Thr Pro Phe Leu Ser Val Thr Phe Phe Asn Leu Ser Ile Tyr Leu Asn
    210                 215                 220

Ile Gln Arg Arg Thr Arg Leu Arg Leu Asp Gly Gly Arg Glu Ala Gly
225                 230                 235                 240

Pro Glu Pro Pro Pro Asp Ala Gln Pro Ser Pro Pro Ala Pro Pro
                245                 250                 255

Ser Cys Trp Gly Cys Trp Pro Lys Gly His Gly Glu Ala Met Pro Leu
            260                 265                 270

His Arg Tyr Gly Val Gly Glu Ala Gly Pro Gly Val Glu Ala Gly Glu
        275                 280                 285

```
Ala Ala Leu Gly Gly Gly Ser Gly Gly Gly Ala Ala Ala Ser Pro Thr
    290                 295                 300

Ser Ser Ser Gly Ser Ser Ser Arg Gly Thr Glu Arg Pro Arg Ser Leu
305                 310                 315                 320

Lys Arg Gly Ser Lys Pro Ser Ala Ser Ser Ala Ser Leu Glu Lys Arg
                325                 330                 335

Met Lys Met Val Ser Gln Ser Ile Thr Gln Arg Phe Arg Leu Ser Arg
            340                 345                 350

Asp Lys Lys Val Ala Lys Ser Leu Ala Ile Ile Val Ser Ile Phe Gly
        355                 360                 365

Leu Cys Trp Ala Pro Tyr Thr Leu Leu Met Ile Ile Arg Ala Ala Cys
    370                 375                 380

His Gly Arg Cys Ile Pro Asp Tyr Trp Tyr Glu Thr Ser Phe Trp Leu
385                 390                 395                 400

Leu Trp Ala Asn Ser Ala Val Asn Pro Val Leu Tyr Pro Leu Cys His
                405                 410                 415

Tyr Ser Phe Arg Arg Ala Phe Thr Lys Leu Leu Cys Pro Gln Lys Leu
            420                 425                 430

Lys Val Gln Pro His Gly Ser Leu Glu Gln Cys Trp Lys
        435                 440                 445

<210> SEQ ID NO 26
<211> LENGTH: 1953
<212> TYPE: DNA
<213> ORGANISM: Rattus norvegicus
<220> FEATURE:
<221> NAME/KEY: CDS
<222> LOCATION: (302)...(1636)

<400> SEQUENCE: 26
agctaggggt gcaccgacgc accgcggcgg ctggagctcg gctttgctct cgctgcagca     60
gccgcgccgc ccgccccact ccgctcagat tccgacacca gccccctctg gatcgccctc    120
ctggactcta gcccgggctc ttgctccgac cccgcggacc atgctccggg cgccccccgg    180
aaaaccgggc tgggcgaaga gccggcaaag attaggctca cgagcggggg ccccacccgg    240
ccacccagct ctccgcccgt gccctgcccg gtgtccccga gccgtgtgag cctgctgggc    300 c atg gag cgc gcg ccg ccc gac ggg ctg atg aac gcg tcg ggc act ctg    349
  Met Glu Arg Ala Pro Pro Asp Gly Leu Met Asn Ala Ser Gly Thr Leu
    1               5                  10                  15 gcc gga gag gcg gcg gct gca ggc ggg gcg cgc ggc ttc tcg gct gcc    397
Ala Gly Glu Ala Ala Ala Gly Gly Ala Arg Gly Phe Ser Ala Ala
                20                  25                  30 tgg acc gct gtc ctg gct gcg ctc atg gcg ctg ctc atc gtg gcc aca    445
Trp Thr Ala Val Leu Ala Ala Leu Met Ala Leu Leu Ile Val Ala Thr
        35                  40                  45 gta ctg ggc aac gcg ctg gtc atg ctc gcc ttc gtg gcg gat tcg agc    493
Val Leu Gly Asn Ala Leu Val Met Leu Ala Phe Val Ala Asp Ser Ser
    50                  55                  60 ctc cgc acc cag aac aac ttc ttt ctg ctc aac ctc gcc atc tcc gac    541
Leu Arg Thr Gln Asn Asn Phe Phe Leu Leu Asn Leu Ala Ile Ser Asp
65                  70                  75                  80 ttc ctc gtg ggt gcc ttc tgc atc cca ttg tac gta ccc tat gtg ctg    589
Phe Leu Val Gly Ala Phe Cys Ile Pro Leu Tyr Val Pro Tyr Val Leu
                85                  90                  95 acc ggc cgt tgg acc ttc ggc cgg ggc ctc tgc aag ctg tgg ctg gtg    637
Thr Gly Arg Trp Thr Phe Gly Arg Gly Leu Cys Lys Leu Trp Leu Val
                100                 105                 110
```

```
                                                                -continued gta gac tac cta ctg tgt gcc tcc tcg gtc ttc aac atc gta ctc atc       685
Val Asp Tyr Leu Leu Cys Ala Ser Ser Val Phe Asn Ile Val Leu Ile
            115                 120                 125 agc tat gac cga ttc ctg tca gtc act cga gct gtc tcc tac agg gcc       733
Ser Tyr Asp Arg Phe Leu Ser Val Thr Arg Ala Val Ser Tyr Arg Ala
130                 135                 140 cag cag ggg gac acg aga cgg gcc gtt cgg aag atg gca ctg gtg tgg       781
Gln Gln Gly Asp Thr Arg Arg Ala Val Arg Lys Met Ala Leu Val Trp
145                 150                 155                 160 gtg ctg gcc ttc ctg ctg tat ggg cct gcc atc ctg agt tgg gag tac       829
Val Leu Ala Phe Leu Leu Tyr Gly Pro Ala Ile Leu Ser Trp Glu Tyr
                165                 170                 175 ctg tct ggt ggc agt tcc atc ccc gag ggc cac tgc tat gct gag ttc       877
Leu Ser Gly Gly Ser Ser Ile Pro Glu Gly His Cys Tyr Ala Glu Phe
            180                 185                 190 ttc tac aac tgg tac ttt ctc atc acg gcc tcc acc ctc gag ttc ttc       925
Phe Tyr Asn Trp Tyr Phe Leu Ile Thr Ala Ser Thr Leu Glu Phe Phe
        195                 200                 205 acg ccc ttc ctc agc gtt acc ttc ttc aac ctc agc atc tac ctg aac       973
Thr Pro Phe Leu Ser Val Thr Phe Phe Asn Leu Ser Ile Tyr Leu Asn
210                 215                 220 atc cag agg cgc acc cgc ctt cgg ctt gat ggg ggc cgt gag gct ggc      1021
Ile Gln Arg Arg Thr Arg Leu Arg Leu Asp Gly Gly Arg Glu Ala Gly
225                 230                 235                 240 cca gaa ccc cca cca gat gcc cag ccc tcg cca cct cca gct ccc ccc      1069
Pro Glu Pro Pro Pro Asp Ala Gln Pro Ser Pro Pro Pro Ala Pro Pro
                245                 250                 255 agc tgc tgg ggc tgc tgg cca aaa ggg cat ggc gag gcc atg ccg ttg      1117
Ser Cys Trp Gly Cys Trp Pro Lys Gly His Gly Glu Ala Met Pro Leu
            260                 265                 270 cac agg tat ggg gtg ggt gag gca ggc cct ggt gtt gag gct ggg gag      1165
His Arg Tyr Gly Val Gly Glu Ala Gly Pro Gly Val Glu Ala Gly Glu
        275                 280                 285 gct gcc ctc ggg ggt ggc agt ggt gga ggt gct gct gcc tcg ccc acc      1213
Ala Ala Leu Gly Gly Gly Ser Gly Gly Gly Ala Ala Ala Ser Pro Thr
290                 295                 300 tcc agc tct ggc agc tcc tca agg ggc act gag agg cca cgc tca ctc      1261
Ser Ser Ser Gly Ser Ser Ser Arg Gly Thr Glu Arg Pro Arg Ser Leu
305                 310                 315                 320 aaa agg ggc tcc aag cca tca gca tct tca gca tcc ctg gag aag cgc      1309
Lys Arg Gly Ser Lys Pro Ser Ala Ser Ser Ala Ser Leu Glu Lys Arg
                325                 330                 335 atg aag atg gtg tcc cag agc atc acc cag cgc ttc cgg ctg tcg cgg      1357
Met Lys Met Val Ser Gln Ser Ile Thr Gln Arg Phe Arg Leu Ser Arg
            340                 345                 350 gac aag aag gtg gcc aag tcg ctg gcc atc atc gtg agc atc ttt ggg      1405
Asp Lys Lys Val Ala Lys Ser Leu Ala Ile Ile Val Ser Ile Phe Gly
        355                 360                 365 ctc tgc tgg gcg ccg tac acg ctc cta atg atc atc cga gct gct tgc      1453
Leu Cys Trp Ala Pro Tyr Thr Leu Leu Met Ile Ile Arg Ala Ala Cys
370                 375                 380 cat ggc cgc tgc atc ccc gat tac tgg tac gag acg tcc ttc tgg ctt      1501
His Gly Arg Cys Ile Pro Asp Tyr Trp Tyr Glu Thr Ser Phe Trp Leu
385                 390                 395                 400 ctg tgg gcc aac tcg gcc gtc aac ccc gtc ctc tac cca ctg tgc cac      1549
Leu Trp Ala Asn Ser Ala Val Asn Pro Val Leu Tyr Pro Leu Cys His
                405                 410                 415 tac agc ttc cgc aga gcc ttc acc aag ctc ctc tgc ccc cag aag ctc      1597
Tyr Ser Phe Arg Arg Ala Phe Thr Lys Leu Leu Cys Pro Gln Lys Leu
            420                 425                 430
```

```
aag gtc cag ccc cac ggc tcc ctg gag cag tgc tgg aag tgagcagctg    1646
Lys Val Gln Pro His Gly Ser Leu Glu Gln Cys Trp Lys
        435                 440                 445 ccccaccctt ctgaggccag gcccttgtac ttgtttgagt gggcagccgg agcgtgggcg  1706
gggccctggt ccatgctccg ctccaaatgc catggcggcc tcttagatca tcaaccccgc  1766
agtggggtag catggcaggt gggccaagag ccctagttgg tggagctaga gtgtgctggt  1826
tagctctgcc gcacattctc cttcaccaca cagaagagac aatccaggag tcccaggcat  1886
gccttcacct acacacacac acacacacac acacacacac acaccacagt gcagtgccag  1946
tgatgtc                                                            1953
```